(12) United States Patent
Lambrecht et al.

(10) Patent No.: US 7,507,243 B2
(45) Date of Patent: Mar. 24, 2009

(54) DEVICES AND METHOD FOR AUGMENTING A VERTEBRAL DISC

(76) Inventors: Gregory Lambrecht, 220 Eliot St., Natick, MA (US) 01760; Jason Partin, 50 Lake St., Unit N, Winchester, MA (US) 01890; Sean Kavanaugh, Hatties Way, Eastham, MA (US) 02642; Jacob Einhorn, 55 Verndale St., Brookline, MA (US) 02446

(*) Notice: Subject to any disclaimer, the term of this patent is extended or adjusted under 35 U.S.C. 154(b) by 0 days.

(21) Appl. No.: 10/430,902

(22) Filed: May 7, 2003

(65) Prior Publication Data
US 2004/0097924 A1 May 20, 2004

Related U.S. Application Data

(63) Continuation-in-part of application No. 10/055,504, filed on Oct. 25, 2001, which is a continuation-in-part of application No. 09/696,636, filed on Oct. 25, 2000, now Pat. No. 6,508,839, which is a continuation-in-part of application No. 09/642,450, filed on Aug. 18, 2000, now Pat. No. 6,482,235, which is a continuation-in-part of application No. 09/608,797, filed on Jun. 30, 2000, now Pat. No. 6,425,919.

(60) Provisional application No. 60/439,261, filed on Jan. 10, 2003, provisional application No. 60/438,022, filed on Jan. 3, 2003, provisional application No. 60/417,219, filed on Oct. 9, 2002, provisional application No. 60/311,586, filed on Aug. 10, 2001, provisional application No. 60/172,996, filed on Dec. 19, 1999, provisional application No. 60/161,085, filed on Oct. 25, 1999, provisional application No. 60/149,490, filed on Aug. 18, 1999.

(51) Int. Cl.
*A61B 17/54* (2006.01)
*A61B 17/60* (2006.01)
*A61F 2/00* (2006.01)

(52) U.S. Cl. .......................... 606/99; 606/92

(58) Field of Classification Search ... 623/17.11–17.16; 604/60; 606/92–94, 99, 213
See application file for complete search history.

(56) References Cited

U.S. PATENT DOCUMENTS 3,526,567 A 9/1970 Macone (Continued)

FOREIGN PATENT DOCUMENTS

EP 0277678 8/1988

(Continued)

OTHER PUBLICATIONS

Ahlgren, B.D., et al., "Anular Incision Technique on the Strength and Multidirectional Flexibility of the Healing Intervertebral Disc," *Spine*, 19 (8) : 948-954 (1994).

(Continued)

*Primary Examiner*—Bruce E Snow
(74) *Attorney, Agent, or Firm*—Knobbe, Martens, Olson & Bear, LLP;; Sean Kavanaugh

(57) ABSTRACT

A vertebral disc prosthesis, a method of implanting a prosthesis and a deployment device is provided. The prosthesis may be implanted into the interior region of the vertebral disc so as to displace existing vertebral tissue, such as NP. The size or amount of the prosthesis inserted into the interior region of the vertebral disc may be a characteristic of the disc or the prosthesis. For example, the amount or size of prosthesis inserted into the disc may be dependent upon restoring the functionality of the disc (e.g., the ability of the disc to transfer nutrients or otherwise survive, the ability of the disc to carry the required loads and absorb stress or the reduction of pain). Restoring disc function may be determined by the resulting disc height desired, the resulting disc pressure desired or the resulting disc volume desired. The prosthesis may be sized or positioned within the interior of the vertebral disc such that it is spaced from at least one of the end plates of the vertebral disc. The prosthesis may be formed of a material having a compression strength that is less than 4 mn/m$^2$. A deployment device may be used to facilitate placement of the prosthesis within the vertebral disc. The prosthesis may include a grouping of multiple components that can be deployed as group.

9 Claims, 31 Drawing Sheets

U.S. PATENT DOCUMENTS

| | | |
|---|---|---|
| 3,867,728 A | 2/1975 | Stubstad et al. |
| 3,875,595 A | 4/1975 | Froning |
| 3,921,632 A * | 11/1975 | Bardani .................. 604/891.1 |
| 4,349,921 A | 9/1982 | Kuntz |
| 4,473,070 A | 9/1984 | Matthews et al. |
| 4,502,161 A | 3/1985 | Wall |
| 4,532,926 A | 8/1985 | O'Holla |
| 4,665,906 A | 5/1987 | Jervis |
| 4,741,330 A | 5/1988 | Hayhurst |
| 4,744,364 A | 5/1988 | Kensey |
| 4,772,287 A | 9/1988 | Ray et al. |
| 4,781,190 A | 11/1988 | Lee |
| 4,798,205 A | 1/1989 | Bonomo et al. |
| 4,821,942 A | 4/1989 | Richards et al. |
| 4,837,285 A | 6/1989 | Berg et al. |
| 4,852,568 A | 8/1989 | Kensey |
| 4,863,477 A | 9/1989 | Monson |
| 4,871,094 A * | 10/1989 | Gall et al. .................. 222/386 |
| 4,873,976 A | 10/1989 | Schreiber |
| 4,890,612 A | 1/1990 | Kensey |
| 4,904,260 A | 2/1990 | Ray et al. |
| 4,911,718 A | 3/1990 | Lee et al. |
| 4,917,704 A | 4/1990 | Frey et al. |
| 4,919,667 A | 4/1990 | Richmond |
| 4,932,969 A | 6/1990 | Frey et al. |
| 4,946,378 A | 8/1990 | Hirayama et al. |
| 4,955,908 A | 9/1990 | Frey et al. |
| 5,002,576 A | 3/1991 | Fuhrmann et al. |
| 5,021,059 A | 6/1991 | Kensey et al. |
| 5,035,716 A | 7/1991 | Downey |
| 5,047,055 A | 9/1991 | Bao et al. |
| 5,053,046 A | 10/1991 | Janese |
| 5,059,206 A | 10/1991 | Winters |
| 5,061,274 A | 10/1991 | Kensey |
| 5,071,437 A | 12/1991 | Steffee |
| 5,100,422 A | 3/1992 | Berguer et al. |
| 5,108,420 A | 4/1992 | Marks |
| 5,108,438 A | 4/1992 | Stone |
| 5,116,357 A | 5/1992 | Eberbach |
| 5,122,155 A | 6/1992 | Eberbach |
| 5,123,926 A | 6/1992 | Pisharodi |
| 5,129,906 A | 7/1992 | Ross et al. |
| 5,141,515 A | 8/1992 | Eberbach |
| 5,147,374 A | 9/1992 | Fernandez |
| 5,171,252 A | 12/1992 | Friedland |
| 5,171,259 A | 12/1992 | Inoue |
| 5,171,280 A | 12/1992 | Baumgartner |
| 5,171,281 A | 12/1992 | Parsons et al. |
| 5,176,692 A | 1/1993 | Wilk et al. |
| 5,189,789 A | 3/1993 | Hall |
| 5,192,300 A | 3/1993 | Fowler |
| 5,192,301 A | 3/1993 | Kamiya et al. |
| 5,192,326 A | 3/1993 | Bao et al. |
| 5,201,729 A | 4/1993 | Hertzmann et al. |
| 5,207,649 A | 5/1993 | Aruny |
| 5,219,359 A | 6/1993 | McQuilkin et al. |
| 5,222,974 A | 6/1993 | Kensey et al. |
| 5,239,982 A | 8/1993 | Trauthen |
| 5,242,448 A | 9/1993 | Pettine et al. |
| 5,254,133 A | 10/1993 | Seid |
| 5,258,000 A | 11/1993 | Gianturco |
| 5,258,043 A | 11/1993 | Stone |
| 5,269,783 A | 12/1993 | Sander |
| 5,282,827 A | 2/1994 | Kensey et al. |
| 5,292,332 A | 3/1994 | Lee |
| 5,306,311 A | 4/1994 | Stone et al. |
| 5,312,435 A | 5/1994 | Nash et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,356,432 A | 10/1994 | Rutkow et al. |
| 5,366,460 A | 11/1994 | Eberback |
| 5,368,602 A | 11/1994 | de la Torre |
| 5,370,697 A | 12/1994 | Baumgartner |
| 5,383,477 A | 1/1995 | DeMatteis |
| 5,383,905 A | 1/1995 | Golds et al. |
| 5,397,331 A | 3/1995 | Himpens et al. |
| 5,397,332 A | 3/1995 | Kammerer et al. |
| 5,397,355 A | 3/1995 | Marin et al. |
| 5,405,360 A | 4/1995 | Tovey |
| 5,425,773 A | 6/1995 | Boyd et al. |
| 5,437,631 A | 8/1995 | Janzen |
| 5,445,639 A | 8/1995 | Kuslich et al. |
| 5,456,720 A | 10/1995 | Schultz et al. |
| 5,464,407 A | 11/1995 | McGuire |
| 5,500,000 A | 3/1996 | Feagin et al. |
| 5,507,754 A | 4/1996 | Green et al. |
| 5,514,130 A | 5/1996 | Baker |
| 5,514,180 A | 5/1996 | Heggeness et al. |
| 5,520,700 A | 5/1996 | Beyar et al. |
| 5,522,898 A | 6/1996 | Bao |
| 5,531,759 A | 7/1996 | Kensey et al. |
| 5,534,028 A | 7/1996 | Bao et al. |
| 5,534,030 A | 7/1996 | Navarro et al. |
| 5,545,178 A | 8/1996 | Kensey et al. |
| 5,545,229 A | 8/1996 | Parsons et al. |
| 5,549,617 A | 8/1996 | Green et al. |
| 5,549,679 A | 8/1996 | Kuslich |
| 5,552,100 A | 9/1996 | Shannon et al. |
| 5,556,428 A | 9/1996 | Shah |
| 5,556,429 A | 9/1996 | Felt |
| 5,562,689 A | 10/1996 | Green et al. |
| 5,562,736 A | 10/1996 | Ray et al. |
| 5,562,738 A | 10/1996 | Boyd et al. |
| 5,569,252 A | 10/1996 | Justin et al. |
| 5,571,189 A | 11/1996 | Kuslich |
| 5,582,616 A | 12/1996 | Bolduc et al. |
| 5,591,204 A | 1/1997 | Jansen et al. |
| 5,591,223 A | 1/1997 | Lock et al. |
| 5,613,974 A | 3/1997 | Andreas et al. |
| 5,620,012 A | 4/1997 | Benderev et al. |
| 5,624,463 A | 4/1997 | Stone et al. |
| 5,626,613 A | 5/1997 | Schmieding |
| 5,634,931 A | 6/1997 | Kugel |
| 5,634,936 A | 6/1997 | Linden et al. |
| 5,641,373 A | 6/1997 | Shannon et al. |
| 5,645,084 A | 7/1997 | McKay |
| 5,645,597 A | 7/1997 | Krapiva |
| 5,658,343 A | 8/1997 | Hauselmann et al. |
| 5,662,683 A | 9/1997 | Kay |
| 5,669,935 A | 9/1997 | Rosenman et al. |
| 5,674,294 A | 10/1997 | Bainville et al. |
| 5,674,295 A | 10/1997 | Ray et al. |
| 5,674,296 A | 10/1997 | Bryan et al. |
| 5,676,698 A | 10/1997 | Janzen et al. |
| 5,676,701 A | 10/1997 | Yuan et al. |
| 5,681,351 A | 10/1997 | Jamiolkowski et al. |
| 5,683,465 A | 11/1997 | Shinn et al. |
| 5,690,674 A | 11/1997 | Diaz |
| 5,695,525 A | 12/1997 | Mulhauser et al. |
| 5,702,450 A | 12/1997 | Bisserie |
| 5,702,451 A | 12/1997 | Biedermann et al. |
| 5,702,454 A | 12/1997 | Baumgartner |
| 5,702,462 A | 12/1997 | Oberlander |
| 5,705,780 A | 1/1998 | Bao |
| 5,716,408 A | 2/1998 | Eldridge et al. |
| 5,716,409 A | 2/1998 | Debbas |
| 5,716,413 A | 2/1998 | Walter et al. |
| 5,716,416 A | 2/1998 | Lin |
| 5,725,577 A | 3/1998 | Saxon |
| 5,728,150 A | 3/1998 | McDonald et al. |
| 5,730,744 A | 3/1998 | Justin et al. |
| 5,733,337 A | 3/1998 | Carr, Jr. et al. |

| | | | | | | |
|---|---|---|---|---|---|---|
| 5,743,917 | A | 4/1998 | Saxon | 6,206,921 B1 | 3/2001 | Guagliano et al. |
| 5,746,755 | A | 5/1998 | Wood et al. | 6,214,039 B1 | 4/2001 | Banas et al. |
| 5,746,765 | A | 5/1998 | Kleshinski et al. | 6,224,630 B1 | 5/2001 | Bao et al. |
| 5,755,797 | A | 5/1998 | Baumgartner | 6,224,631 B1 | 5/2001 | Kohrs |
| 5,766,246 | A | 6/1998 | Mulhauser et al. | 6,231,597 B1 | 5/2001 | Deem et al. |
| 5,769,864 | A | 6/1998 | Kugel | 6,244,630 B1 | 5/2001 | Bao et al. |
| 5,769,893 | A | 6/1998 | Shah | 6,241,722 B1 | 6/2001 | Dobak et al. |
| 5,772,661 | A | 6/1998 | Michelson | 6,245,099 B1 | 6/2001 | Edwin et al. |
| 5,776,183 | A | 7/1998 | Kanesaka et al. | 6,245,107 B1 | 6/2001 | Ferree |
| 5,782,844 | A | 7/1998 | Yoon et al. | 6,264,659 B1 | 7/2001 | Ross et al. |
| 5,785,705 | A | 7/1998 | Baker | 6,264,695 B1 | 7/2001 | Stoy |
| 5,800,549 | A | 9/1998 | Bao et al. | 6,267,834 B1 | 7/2001 | Shannon et al. |
| 5,810,851 | A | 9/1998 | Yoon | 6,273,912 B1 | 8/2001 | Scholz et al. |
| 5,823,994 | A | 10/1998 | Sharkey et al. | 6,280,475 B1 | 8/2001 | Bao et al. |
| 5,824,008 | A | 10/1998 | Bolduc et al. | 6,312,462 B1 | 11/2001 | McDermott et al. |
| 5,824,082 | A | 10/1998 | Brown | 6,325,805 B1 | 12/2001 | Oglivie et al. |
| 5,824,093 | A | 10/1998 | Ray et al. | 6,355,063 B1 | 3/2002 | Calcote |
| 5,824,094 | A | 10/1998 | Serhan et al. | 6,371,990 B1 | 4/2002 | Ferree |
| 5,827,298 | A | 10/1998 | Hart et al. | 6,383,214 B1 | 5/2002 | Banas et al. |
| 5,836,315 | A | 11/1998 | Benderev et al. | 6,398,803 B1 | 6/2002 | Layne et al. |
| 5,843,084 | A | 12/1998 | Hart et al. | 6,402,750 B1 | 6/2002 | Atkinson et al. |
| 5,843,173 | A | 12/1998 | Shannon et al. | 6,416,537 B1 | 7/2002 | Martakos et al. |
| 5,846,261 | A | 12/1998 | Kotula et al. | 6,419,704 B1 | 7/2002 | Ferree |
| 5,860,425 | A | 1/1999 | Benderev et al. | 6,425,919 B1 | 7/2002 | Lambrecht et al. |
| 5,860,977 | A | 1/1999 | Zucherman et al. | 6,428,575 B2 | 8/2002 | Koo et al. |
| 5,865,845 | A | 2/1999 | Thalgott | 6,428,576 B1 | 8/2002 | Haldimann |
| 5,865,846 | A | 2/1999 | Bryan et al. | 6,436,143 B1 | 8/2002 | Ross et al. |
| 5,888,220 | A | 3/1999 | Felt et al. | 6,443,988 B2 | 9/2002 | Felt et al. |
| 5,888,226 | A | 3/1999 | Rogozinski | 6,482,235 B1 | 11/2002 | Lambrecht et al. |
| 5,893,889 | A | 4/1999 | Harrington | 6,491,690 B1 | 12/2002 | Goble et al. |
| 5,916,225 | A | 6/1999 | Kugel | 6,503,269 B2 | 1/2003 | Neild et al. |
| 5,919,235 | A | 7/1999 | Husson et al. | 6,508,839 B1 | 1/2003 | Lambrecht et al. |
| 5,922,026 | A | 7/1999 | Chin | 6,520,967 B1 | 2/2003 | Cauthen |
| 5,928,279 | A | 7/1999 | Shannon et al. | 6,530,932 B1 | 3/2003 | Swayze et al. |
| 5,928,284 | A | 7/1999 | Mehdizadeh | 6,530,933 B1 | 3/2003 | Yeung et al. |
| 5,935,147 | A | 8/1999 | Kensey et al. | 6,579,291 B1 | 6/2003 | Keith et al. |
| 5,954,716 | A | 9/1999 | Sharkey et al. | 6,592,625 B2 | 7/2003 | Cauthen |
| 5,954,767 | A | 9/1999 | Pajotin et al. | 6,648,915 B2 | 11/2003 | Sazy |
| 5,957,939 | A | 9/1999 | Heaven et al. | 6,712,853 B2 | 3/2004 | Kuslich |
| 5,961,545 | A | 10/1999 | Lentz et al. | 6,719,797 B1 | 4/2004 | Ferree |
| 5,972,000 | A | 10/1999 | Beyar et al. | 6,726,696 B1 | 4/2004 | Houser et al. |
| 5,972,007 | A | 10/1999 | Sheffield et al. | 6,749,605 B2 | 6/2004 | Ashley et al. |
| 5,972,022 | A | 10/1999 | Huxel | 6,783,546 B2 | 8/2004 | Zucherman et al. |
| 5,976,174 | A | 11/1999 | Ruiz | 6,805,695 B2 | 10/2004 | Keith et al. |
| 5,976,186 | A | 11/1999 | Bao et al. | 6,821,276 B2 | 11/2004 | Lambrecht et al. |
| 5,976,192 | A | 11/1999 | McIntyre et al. | 6,855,166 B2 | 2/2005 | Kohrs |
| 5,980,504 | A | 11/1999 | Sharkey et al. | 6,883,520 B2 | 4/2005 | Lambrecht et al. |
| 6,001,056 | A | 12/1999 | Jassawalla et al. | 6,932,841 B2 | 8/2005 | Skylar et al. |
| 6,001,130 | A | 12/1999 | Bryan et al. | 6,936,072 B2 | 8/2005 | Lambrecht et al. |
| 6,007,570 | A | 12/1999 | Sharkey et al. | 6,969,404 B2 | 11/2005 | Ferree |
| 6,007,575 | A | 12/1999 | Samuels | 7,033,393 B2 | 4/2006 | Gainer et al. |
| 6,019,793 | A | 2/2000 | Perren et al. | 7,052,516 B2 | 5/2006 | Cauthen, III et al. |
| 6,024,096 | A | 2/2000 | Buckberg | 7,094,258 B2 | 8/2006 | Lambrecht et al. |
| 6,027,527 | A | 2/2000 | Asano et al. | 7,124,761 B2 | 10/2006 | Lambrecht et al. |
| 6,073,051 | A | 6/2000 | Sharkey et al. | 7,144,397 B2 | 12/2006 | Lambrecht et al. |
| 6,096,044 | A | 8/2000 | Boyd et al. | 7,163,561 B2 | 1/2007 | Michelson |
| 6,099,791 | A | 8/2000 | Shannon et al. | 7,198,047 B2 | 4/2007 | Lambrecht et al. |
| 6,102,930 | A | 8/2000 | Simmons, Jr. | 7,201,776 B2 | 4/2007 | Ferree et al. |
| 6,105,581 | A | 8/2000 | Eggers et al. | 7,220,281 B2 | 5/2007 | Lambrecht et al. |
| 6,113,639 | A | 9/2000 | Ray et al. | 7,223,289 B2 | 5/2007 | Trieu et al. |
| 6,120,539 | A | 9/2000 | Eldridge et al. | 7,258,700 B2 | 8/2007 | Lambrecht et al. |
| 6,124,523 | A | 9/2000 | Banas et al. | 2001/0004710 A1 | 6/2001 | Felt et al. |
| 6,126,682 | A | 10/2000 | Sharkey et al. | 2001/0031963 A1 | 10/2001 | Sharkey et al. |
| 6,132,465 | A | 10/2000 | Ray et al. | 2002/0007218 A1 | 1/2002 | Cauthen |
| 6,140,452 | A | 10/2000 | Felt et al. | 2002/0045942 A1 | 4/2002 | Ham |
| 6,146,380 | A | 11/2000 | Racz et al. | 2002/0049498 A1 | 4/2002 | Yuksel et al. |
| 6,153,292 | A | 11/2000 | Bell et al. | 2002/0111688 A1 | 8/2002 | Cauthen |
| 6,174,311 | B1 | 1/2001 | Branch et al. | 2002/0120337 A1 | 8/2002 | Cauthen |
| 6,179,836 | B1 | 1/2001 | Eggers et al. | 2002/0123807 A1 | 9/2002 | Cauthen, III |
| 6,183,518 | B1 | 2/2001 | Ross et al. | 2002/0147496 A1 | 10/2002 | Belef et al. |
| 6,187,048 | B1 | 2/2001 | Milner et al. | 2002/0151980 A1 | 10/2002 | Cauthen |
| 6,190,353 | B1 | 2/2001 | Makower et al. | 2002/0165542 A1 | 11/2002 | Ferree |
| 6,203,735 | B1 | 3/2001 | Edwin et al. | 2002/0189622 A1 | 12/2002 | Cauthen, III et al. |

| | | |
|---|---|---|
| 2002/0198599 A1 | 12/2002 | Haldimann |
| 2003/0004574 A1 | 1/2003 | Ferree |
| 2003/0040796 A1 | 2/2003 | Ferree |
| 2003/0050702 A1 | 3/2003 | Berger |
| 2003/0074075 A1 | 4/2003 | Thomas, Jr. et al. |
| 2003/0074076 A1 | 4/2003 | Ferree et al. |
| 2003/0078579 A1 | 4/2003 | Ferree |
| 2003/0130738 A1 | 7/2003 | Hovda et al. |
| 2003/0149438 A1 | 8/2003 | Nichols et al. |
| 2003/0158604 A1 | 8/2003 | Cauthen et al. |
| 2004/0002764 A1 | 1/2004 | Gainor et al. |
| 2004/0010317 A1 | 1/2004 | Lambrecht et al. |
| 2004/0024465 A1 | 2/2004 | Lambrecht et al. |
| 2004/0030392 A1 | 2/2004 | Lambrecht et al. |
| 2004/0034429 A1 | 2/2004 | Lambrecht et al. |
| 2004/0044412 A1 | 3/2004 | Lambrecht et al. |
| 2004/0097924 A1 | 5/2004 | Lambrecht et al. |
| 2004/0116922 A1 | 6/2004 | Hovda et al. |
| 2004/0138673 A1 | 7/2004 | Lambrecht et al. |
| 2004/0260238 A1* | 12/2004 | Call .................. 604/97.03 |
| 2004/0260300 A1 | 12/2004 | Gorensek et al. |
| 2004/0260305 A1 | 12/2004 | Gorensek et al. |
| 2004/0260397 A1 | 12/2004 | Lambrecht et al. |
| 2005/0004578 A1 | 1/2005 | Lambrecht et al. |
| 2005/0010205 A1 | 1/2005 | Hovda et al. |
| 2005/0033440 A1 | 2/2005 | Lambrecht et al. |
| 2005/0033441 A1 | 2/2005 | Lambrecht et al. |
| 2005/0038519 A1 | 2/2005 | Lambrecht et al. |
| 2005/0060038 A1 | 3/2005 | Lambrecht et al. |
| 2005/0206959 A1 | 9/2005 | Lambrecht et al. |
| 2006/0030857 A1 | 2/2006 | de Villiers et al. |
| 2006/0129156 A1 | 6/2006 | Cauthen et al. |
| 2006/0161162 A1 | 7/2006 | Lambrecht et al. |
| 2006/0200246 A1 | 9/2006 | Lambrecht et al. |
| 2006/0217812 A1 | 9/2006 | Lambrecht et al. |
| 2006/0282167 A1 | 12/2006 | Lambrecht et al. |
| 2007/0061012 A1 | 3/2007 | Cauthen, III |
| 2007/0067039 A1 | 3/2007 | Lambrecht et al. |
| 2007/0118133 A1 | 5/2007 | Lambrecht et al. |
| 2007/0118226 A1 | 5/2007 | Lambrecht et al. |
| 2007/0156244 A1 | 7/2007 | Cauthen |
| 2007/0185497 A1 | 8/2007 | Cauthen et al. |

FOREIGN PATENT DOCUMENTS

| | | |
|---|---|---|
| EP | 0298233 | 1/1989 |
| EP | 0298235 | 1/1989 |
| EP | 0 700 671 A1 | 3/1996 |
| EP | 0722700 | 12/1998 |
| EP | 1091776 | 5/2004 |
| EP | 1214026 | 4/2005 |
| EP | 1180978 | 5/2005 |
| FR | 2639823 A1 | 6/1990 |
| JP | S63-95043 | 4/1988 |
| JP | S64-887 | 1/1989 |
| JP | H05-29694 | 7/1993 |
| RU | 2020901 | 10/1994 |
| RU | 93031998 A | 11/1995 |
| RU | 2055544 | 3/1996 |
| RU | 2078551 | 5/1997 |
| RU | 96121354 A | 1/1999 |
| WO | WO 92/10982 | 9/1992 |
| WO | WO 95/26689 | 10/1995 |
| WO | WO 95/31946 | 11/1995 |
| WO | WO 95/34331 | 12/1995 |
| WO | WO96/01164 | 1/1996 |
| WO | WO 96/01598 | 1/1996 |
| WO | WO 97/26847 | 7/1997 |
| WO | WO97/30638 | 8/1997 |
| WO | WO98/17190 | 4/1998 |
| WO | WO 98/20939 | 5/1998 |
| WO | WO98/34552 | 8/1998 |
| WO | WO 98/38918 | 9/1998 |
| WO | WO99/00074 | 1/1999 |
| WO | WO 99/02108 | 1/1999 |
| WO | WO99/02214 | 1/1999 |
| WO | WO99/03422 | 1/1999 |
| WO | WO99/30651 | 6/1999 |
| WO | WO99/47058 | 9/1999 |
| WO | WO 99/61084 | 9/1999 |
| WO | WO99/62439 | 12/1999 |
| WO | WO 00/14708 | 3/2000 |
| WO | WO 00/18328 | 4/2000 |
| WO | WO00/42953 | 7/2000 |
| WO | WO 00/44288 | 8/2000 |
| WO | WO 00/45741 | 8/2000 |
| WO | WO 00/49978 | 8/2000 |
| WO | WO00/62832 | 10/2000 |
| WO | WO00/71043 | 11/2000 |
| WO | WO 01/10316 | 2/2001 |
| WO | WO 01/12080 | 2/2001 |
| WO | WO 01/12107 | 2/2001 |
| WO | WO01/21246 | 3/2001 |
| WO | WO 01/28464 | 4/2001 |
| WO | WO 01/28468 A1 | 4/2001 |
| WO | WO 01/39696 | 6/2001 |
| WO | WO01/45579 | 6/2001 |
| WO | WO 01/52914 | 7/2001 |
| WO | WO 01/45577 | 6/2002 |
| WO | WO 02/051622 | 7/2002 |
| WO | WO 02/058599 A2 | 8/2002 |
| WO | WO 02/067824 A2 | 9/2002 |
| WO | WO03/039328 | 5/2003 |
| WO | WO03/088876 | 10/2003 |

OTHER PUBLICATIONS

Bagga C.S., Williams P., Highma P.A., Bao B.Q., "Development of Fatigue Test Model for a Spinal Nucleus Prothesis with Preliminary Results for a Hydrogel Spinal Prosthetic Nucleus," Proceedings of the 1997 Bioengineering Conference, 441-442: BED-vol. 35, Sunriver, Oregon, Jun. 11-15, 1997.

Balderston, R.A., et al., "The Treatment of Lumbar Disc Herniation: Simple Fragment Excision Versus Disc Space Curettage," *J. of Spinal Disorders*, 4 (1) : 22-25 (1991).

Bao Q.B., Bagga C.S., "The Dynamic Mechanical Analysis of Hydrogel Elastomers," Thermochimica Acta, 226:107-113 (1993).

Bao Q.B., McCullen G.M., Higham P.A., Dumbleton J.H., Yuan H.A., "The Artificial Disc: Theory, Design and Materials," Biomaterials, vol. 17, No. 12:1157-1167 (1996).

Bao Q.B., Yuan H.A., "Artificial Disc Technology," Neurosurg Focus 9(4), 2000.

Barr, J.S., "Ruptured Intervertebral Disc and Sciatic Pain," *J. of Bone and Joint Surgery*, 29, (2) : 429-437 (1947).

Brinckmann, P., et al., "Change of Disc Height, Radial Disc Bulge, and Intradiscal Pressure From Discectomy An in Vitro Investigation on Human Lumbar Discs," *Spine*, 16 (6) : 641-646 (1991).

Goel, V.K., et al., "Mechanical Properties of Lumbar Spinal Motion Segments as Affected by Partial Disc Removal," *Spine*, 11 (10) : 1008-1012 (1986).

Hanley, E. N., Jr., et al., "The Development of Low-Back Pain After Excision of a Lumbar Disc," *J. of Bone and Joint Surgery*, 71A (5) : 719-721 (1989).

Hedman T. P., Kostuik J.P., Fernie G.R., Hellier W.G., "Design of an Intervertebral Disc Prosthesis," Spine 16 (Suppl. 6):S256-S260 (1991).

Heggeness, M.H., et al., "Discography of Lumbar Discs After Surgical Treatment for Disc Herniation," *Spine*, 22 (14) : 1606-1609 (1997).

Husson J.L., Baumgartner W., Le Huec J.C., "Nucléoplastie Inter-Somatique Par Voie Postérieure Per-Dissectomie: Concept et Étude Expérimentale," Restabilisation Inter-Somatique Due Rachis Lombaire:311-320 (1996).

Husson J.L., Scharer N., Le Nihouannen J.C., Freudiger S., Baumgartner W., Polard J.L., "Nucleoplasty During Discectomy Concept and Experimental Study," Rachis vol. 9, No. 3:145-152 (1997).

Kayama, S., et al., "Incision of the Anulus Fibrosus Induces Nerve Root Morphologic, Vascular, and Functional Changes," *Spine*, 21 (22) : 2539-2543 (1996).

Khelimsky et al. "Plastic Surgery of Damaged Intervertebral Discs with Fast-Solidifying Glue Composition (Experimental Research)." Collected articles Experimental Traumatic Surgery and Orthopaedics Moscow, 1990, pp. 88-90.

Langrana N.A., Parsons J.R., Lee C.K., Vuono-Hawkins M., Yang S.W., Alexander H., "Materials and Design Concepts for an Intervertebral Disc Spacer. I. Fiber-Reinforced Composite Design," Journal of Applied Biomaterials, vol. 4:125-132 (1994).

Lemaire J.P., Skalli W., Lavaste F., Templier A., Mendes, F., Diop A., Sauty V., Laloux E., "Intervertebral Disc Prosthesis," Clinical Orthopaedics and Related Research, No. 337:64-76 (1997).

Martz E.O., Goel V.K., Pope M.H., Park J.B., "Materials and Design of Spinal Implants—A Review," Journal of Biomedical Materials Research, vol. 38, Issue 3:267-288 (1997).

Postacchini, F., "Spine Update results of Surgery Compared With Conservative Management for Lumbar Disc Herniations," *Spine*, 21 (11) : 1383-1387 (1996).

Ray C.D., Schonmayr R., Kavanagh S.A., Assell R., "Prosthetic Disc Nucleus Implants," Riv. Neuroradiol 1999:12 (Suppl. 1):157-162.

Rogers, L.A., "Experimental with Limited versus Extensive Disc Removal in Patients Undergoing Microsurgical Operations for Ruptured Lumbar Discs," *Neurosurgery*, 22, (1) : 82-85 (1988).

Sakalkale D.P., Bhagia S.A., Slipman C.W., "A Historical Review and Current Perspective on the Intervertebral Disc Prosthesis," Pain Physician, vol. 6, No. 2:1-4 (2003).

Schonmayr R., Busch C., Lotz C., Lotz-Metz G., "Prosthetic Disc Nucleus Implants: The Wiesbaden Feasibility Study, 2 Years follow-up in Ten patients," Riv. Neuroradiol 1999:12 (Suppl. 1):163-170.

Sheljakin S. Ju. "Percutaneous Diskectomy Skin-through Discectomy in Complex Treatment of Patients with Disc Lumbosacral Polyraduculitis." Abstract of a thesis, St. Petersburg, 1996.

Shul'man Kh.M. "Pathogenetic Therapy of Compression Type Osteochondritis of Spinal Lumbar Region." Collected articles Reconstruction-and-Restoration Treatment in Traumatic Surgery, Orthopaedics, Surgery and Neurosurgery, Kazan', 1976, pp. 17-21.

Shul'man Kh.M. "Surgical Treatment of Compression Type Osteochondritis of Spinal Lumbar Region with Intervertebral Disc Implantation." Kazan', 1980, pp. 174-185.

Shul'man Kh.M., Danilov V.I. "Biochemical Experimental Basis of Intervertebral Disc Prosthesis Implantation Method by Fast-solidifying Polyurethane CKYu-PFL in Case of Disc Degeneration or Traumatic Damage." Collected articles Reconstruction-and-Restoration Treatment in Traumatic Surgery, Orthopaedics, Surgery and Neurosurgery. Kazan', 1976, pp. 22-27.

Tibrewal, S.B., et al., "Lumbar Intervertebral Disc Heights in Normal Subjects and Patients with Disc Herniation," *Spine*, 10 (5) : 452-454 (1985).

Tullberg, T., et al., "Radiographic Changes After Lumbar Discectomy," *Spine*, 18 (7) : 843-850 (1993).

Usmanov M.M. "Intervertebral Disc Changes at Local Damage of its Elements and Implantation of Various Materials." Abstract of a thesis Moscow, 1991.

USSR Author's Certificate No. 1477390 "Method for Treatment of Osteochondritis." Published May 17, 1989.

USSR Author's Certificate No. 1827204 "Method for Treatment of Spinal Osteochondritis." Published May 15, 1993.

Yasargil, M.G., "Microsurgical Operation of Herniated Lumbar Disc," p. 81.

Zelentsov E.V. "Plastic Surgery with Collagen of Intervertebral Discs for Surgical Treatment of Lumbosacral Polyradiculitis." Abstract of a thesis, Leningrad, 1990.

Zelentsov E.V. et al. "Application of Collagen for Experimental Plastic Surgery of Intervertebral Discs." Collected articles Integrated Treating of Pain Syndromes of Neurogenic Origin, Leningrad 1984 pp. 86-90.

\* cited by examiner

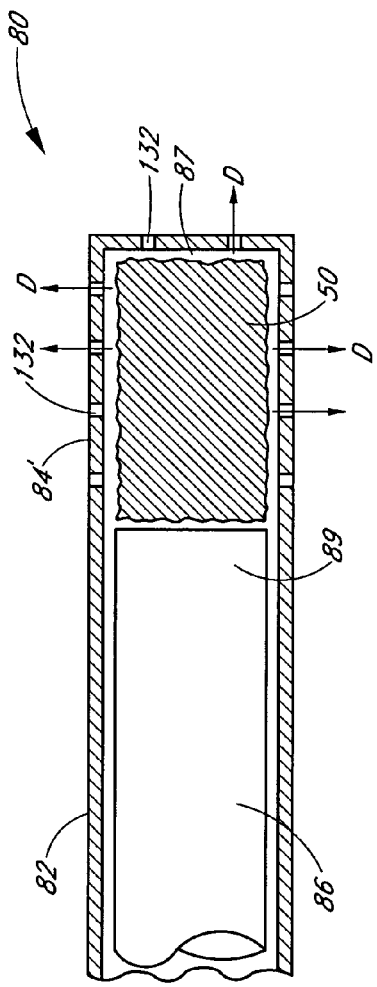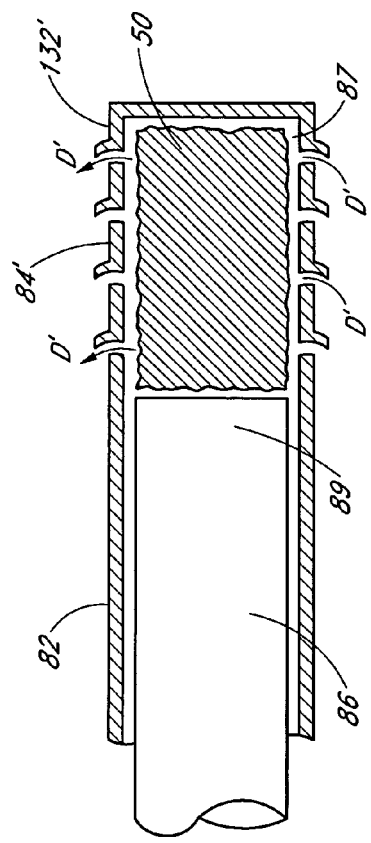
FIG. 20A
FIG. 20B

DEVICES AND METHOD FOR AUGMENTING A VERTEBRAL DISC

RELATED APPLICATIONS

This application claims the benefit of U.S. Provisional Application Ser. Nos. 60/439,261, filed on Jan. 10, 2003; 60/438,022, filed on Jan. 3, 2003; and 60/417,219, filed Oct. 9, 2002.

This application is also a continuation-in-part of U.S. application Ser. No. 10/055,504 filed on Oct. 25, 2001, now pending, which is a continuation-in-part of U.S. application Ser. No. 09/696,636 filed on Oct. 25, 2000, now U.S. Pat. No. 6,508,839, which is a continuation-in-part of U.S. application Ser. No. 09/642,450 filed on Aug. 18, 2000, now U.S. Pat. No. 6,482,235, which is a continuation-in-part of U.S. application Ser. No. 09/608,797 filed on Jun. 30, 2000, now U.S. Pat. No. 6,425,919.

Application Ser. No. 10/055,504 claims the benefit of U.S. Provisional Application Ser. No. 60/311,586 filed on Aug. 10, 2001. application Ser. Nos. 09/642,450 and 09/608,797 each claim the benefit of U.S. Provisional Application Ser. Nos. 60/172,996, filed on Dec. 19, 1999; 60/161,085, filed on Oct. 25, 1999; and 60/149,490 filed Aug. 18, 1999.

Each of these applications is hereby incorporated herein by reference in their entirety.

FIELD OF INVENTION

The present inventions relate generally to treatment of vertebral discs in the lumbar, cervical, or thoracic spine.

DISCUSSION OF RELATED ART

The disc performs the role of absorbing mechanical loads while allowing for constrained flexibility of the spine. The vertebral tissue forming the disc includes a soft, central nucleus pulposus (NP) surrounded by a tough, woven annulus fibrosis (AF) and superior and inferior endplates. Herniation is a result of a weakening in the AF. Symptomatic herniations occur when weakness in the AF allows the NP to bulge or leak, for example, toward the spinal cord and major nerve roots. The most common resulting symptoms are pain radiating along a nerve and low back pain, both of which can be crippling for the patient.

Discectomy has been the most common surgical procedure for treating vertebral disc herniation. This procedure involves removal of disc materials impinging on the nerve roots or spinal cord external to the disc. Depending on the surgeon's preference, varying amounts of NP may also be removed from within the disc space either through the herniation site or through an incision in the AF. This removal of extra NP is commonly done to minimize the risk of recurrent herniation.

SUMMARY OF THE INVENTION

In one embodiment, a vertebral disc prosthesis is provided. The prosthesis includes a mass of material that is adapted to be inserted into the interior region of the vertebral disc. The mass of material has a compressive strength of less than 4 MN/m².

In another embodiment, a prosthesis for implantation into an interior region of a vertebral disc is provided. The vertebral disc includes first and second endplates. The prosthesis includes a mass of material that is adapted for insertion into the interior region of the vertebral disc so as to displace existing vertebral tissue. The mass of material is sized so as to be spaced from both the first and second endplates when implanted into the interior region of the vertebral disc such that the mass of material is surrounded with nucleus pulposus within the interior region of the vertebral disc when implanted therein.

In yet another embodiment, a prosthesis for implantation into an interior region of a vertebral disc is provided. The prosthesis includes an isotropic mass of biocompatible hydrogel having a compressive strength of less than 4 MN/m² and a volume between a range of approximately 0.1 ml and approximately 6.0 ml.

In another embodiment, a method of implanting a prosthesis material into an interior region of a vertebral disc is disclosed. The method includes locating an access site on the disc; inserting, through an opening of the disc at the access site, the prosthesis material into the interior region of the vertebral disc; and monitoring at least one of: a) one or more characteristics of the vertebral disc, and b) one or more characteristics of the prosthesis material.

In still another embodiment, a method of restoring function of a vertebral disc is disclosed. The method includes locating an access site on the disc; and inserting, through an opening of the disc at the access site, a prosthesis material into an interior region of the vertebral disc without removing a substantial amount of nucleus pulposus from the interior region so as to augment existing nucleus pulposus.

In still another embodiment, a method of implanting a prosthesis material into an interior region of a vertebral disc is disclosed. The vertebral disc has first and second endplates. The method includes locating an access site on the disc; inserting, through an opening of the disc at the access site, the prosthesis material into the interior region of the vertebral disc without removing a substantial amount of nucleus pulposus; spacing the prosthesis material from the endplates of the vertebral disc such that the nucleus pulposus substantially surrounds the prosthesis material. The method also includes monitoring at least one of: a) one or more characteristics of the vertebral disc, and b) one or more characteristics of the prosthesis material.

In yet another embodiment, a method of increasing a height of a vertebral disc is disclosed. The method includes locating an access site on the disc; and inserting, through an opening of the disc at the access site, an amount of prosthesis material into an interior region of the vertebral disc without removing a substantial amount of nucleus pulposus from the interior region so as to augment existing nucleus pulposus. The method also includes monitoring the disc height to determine whether a desired disc height is achieved.

In another embodiment, a method of increasing a intradiscal pressure of a vertebral disc is disclosed. The method includes locating an access site on the disc; and inserting, through an opening of the disc at the access site, an amount of prosthesis material into an interior region of the vertebral disc without removing a substantial amount of nucleus pulposus from the interior region so as to augment existing nucleus pulposus. The method also includes monitoring the intradiscal pressure to determine whether a desired intradiscal pressure is achieved.

In still another embodiment, a device for delivering a prosthesis material to an interior region of a vertebral disc is provided. The device includes a body having a proximal end and a distal end and a holder region disposed adjacent the distal end of the body. The holder region being adapted to hold the prosthesis material prior to delivery into the interior region of the vertebral disc. The device further includes a plunger disposed within the body. The plunger and body are adapted to move relative to each other to dispense the prosthesis material. A stop is disposed on the body. The stop is adapted to allow positioning of the body relative to the interior region of the vertebral body such that the prosthesis material can be dispensed within the interior region of the vertebral body at a desired location.

In another embodiment, a device for delivering a prosthesis material to an interior region of a vertebral disc is disclosed. The device includes a body having a proximal end and a flexible distal end. The body defines a longitudinal axis. The flexible distal end is adapted to articulate relative to the axis. A holder region is disposed adjacent the distal end of the body. The holder region is adapted to hold the prosthesis material prior to delivery into the interior region of the vertebral disc. A plunger is disposed within the body. The plunger and body are adapted to move relative to each other to dispense the prosthesis.

In another embodiment, a device for delivering a prosthesis material to an interior region of a vertebral disc is disclosed. The device includes a body having a proximal end and a distal end. The body is formed as a hollow sleeve. A holder region is disposed adjacent the distal end of the body. The holder region is adapted to hold the prosthesis material prior to delivery into the interior region of the vertebral disc. A plunger is axially disposed within the sleeve. The sleeve is adapted to be retracted relative to the plunger to dislodge the prosthesis material from the holder region upon retraction of the sleeve.

In yet another embodiment, a device for delivering a prosthesis material to an interior region of a vertebral disc is disclosed. The device includes a body having a proximal end and a distal end. A holder region is disposed adjacent the distal end. The holder region is adapted to hold the prosthesis material prior to delivery into the interior region of the vertebral disc. The holder region includes a plurality of openings, with each opening adapted to allow prosthesis material to be dispensed from within the holder region. A plunger is disposed within the body. The plunger and body are adapted to move relative to each other to dispense the prosthesis material.

In still another embodiment, a device for delivering a prosthesis material to an interior region of a vertebral disc is disclosed. The device includes a body having a proximal end and a distal end. A holder region is disposed adjacent the distal end of the body. The holder region is adapted to hold the prosthesis material prior to delivery into the interior region of the vertebral disc. A plunger is disposed within the body. The plunger and body are adapted to move relative to each other to dispense the prosthesis material. A gauge cooperates with the device and is adapted to measure the insertion force of the prosthesis material into the inner region of the vertebral disc.

In another embodiment, a method for delivering a prosthesis material into an interior region of a vertebral disc is disclosed. The method includes providing a delivery device having a body having a proximal end and a distal end and a holder region disposed adjacent the distal end. The holder region is adapted to hold the prosthesis material prior to delivery into the interior region of the vertebral disc. The delivery device further including a plunger cooperating with the body. The method further includes loading the holder region with the prosthesis material, advancing at least a portion of the device to a desired location within the vertebral disc, and moving the plunger relative to the body to dislodge the prosthesis material from the device.

In still another embodiment, a kit of parts for use in augmenting vertebral tissue is disclosed. The kit includes a prosthesis according to any of the embodiments described herein; and a device for inserting the prosthesis into the interior region of the vertebral disc.

In yet another embodiment, a kit of parts for use in augmenting vertebral tissue is disclosed, the kit includes a prosthesis adapted for insertion into the vertebral disc; a delivery device for inserting the prosthesis into the interior region of the vertebral disc; and instructions for inserting the prosthesis, the instructions comprising instructions for inserting the prosthesis material into an interior region of the vertebral disc without removing a substantial amount of nucleus pulposus from the disc.

In still another embodiment, a kit of parts for use in augmenting vertebral tissue is disclosed. The kit includes a prosthesis adapted for insertion into the vertebral disc; a delivery device for inserting the prosthesis into the interior region of the vertebral disc; and instructions for inserting the prosthesis. The instructions comprising the any of the methods disclosed herein.

In still another embodiment, a kit of parts for use in augmenting vertebral tissue is disclosed. The kit includes a prosthesis adapted for insertion into the vertebral disc; and a delivery device according to any of the embodiments described herein.

In another embodiment, a vertebral disc prosthesis for displacing nucleus, annulus, or vertebral body endplate tissue of a vertebral disc is disclosed. The prosthesis includes a grouping of at least two discrete components. The grouping is constructed and configured to be inserted together as a group into the interior region of a vertebral disc to displace at least a portion of the nucleus, annulus, or vertebral body endplate tissue.

In yet another embodiment, a method of restoring function of an vertebral disc is disclosed. The vertebral disc has vertebral disc tissue comprising a nucleus, an annulus, and vertebral body endplate tissue. The method includes locating an access site on the vertebral disc; and inserting, at one time, a prosthesis comprising a grouping of at least two discrete components through the access site and into an interior region of the vertebral disc to displace at least a portion of the vertebral disc tissue without removing a substantial amount of nucleus tissue.

Various embodiments of the present invention provide certain advantages and overcome certain drawbacks of prior prostheses. Embodiments of the invention may not share the same advantages, and those that do may not share them under all circumstances. Further features and advantages of the present invention, as well as the structure of various illustrative embodiments, are described in detail below with reference to the accompanying drawings.

BRIEF DESCRIPTION OF THE DRAWINGS

Various embodiments of the invention will now be described, by way of example, with reference to the accompanying drawings, in which:

FIG. 20A is a diagrammatic cross-section representation of a portion of an alternative embodiment of the deployment device;

FIG. 20B is a diagrammatic cross-section representation of a portion of another alternative embodiment of the deployment device;

DESCRIPTION OF ILLUSTRATIVE EMBODIMENTS

Figure 1A:
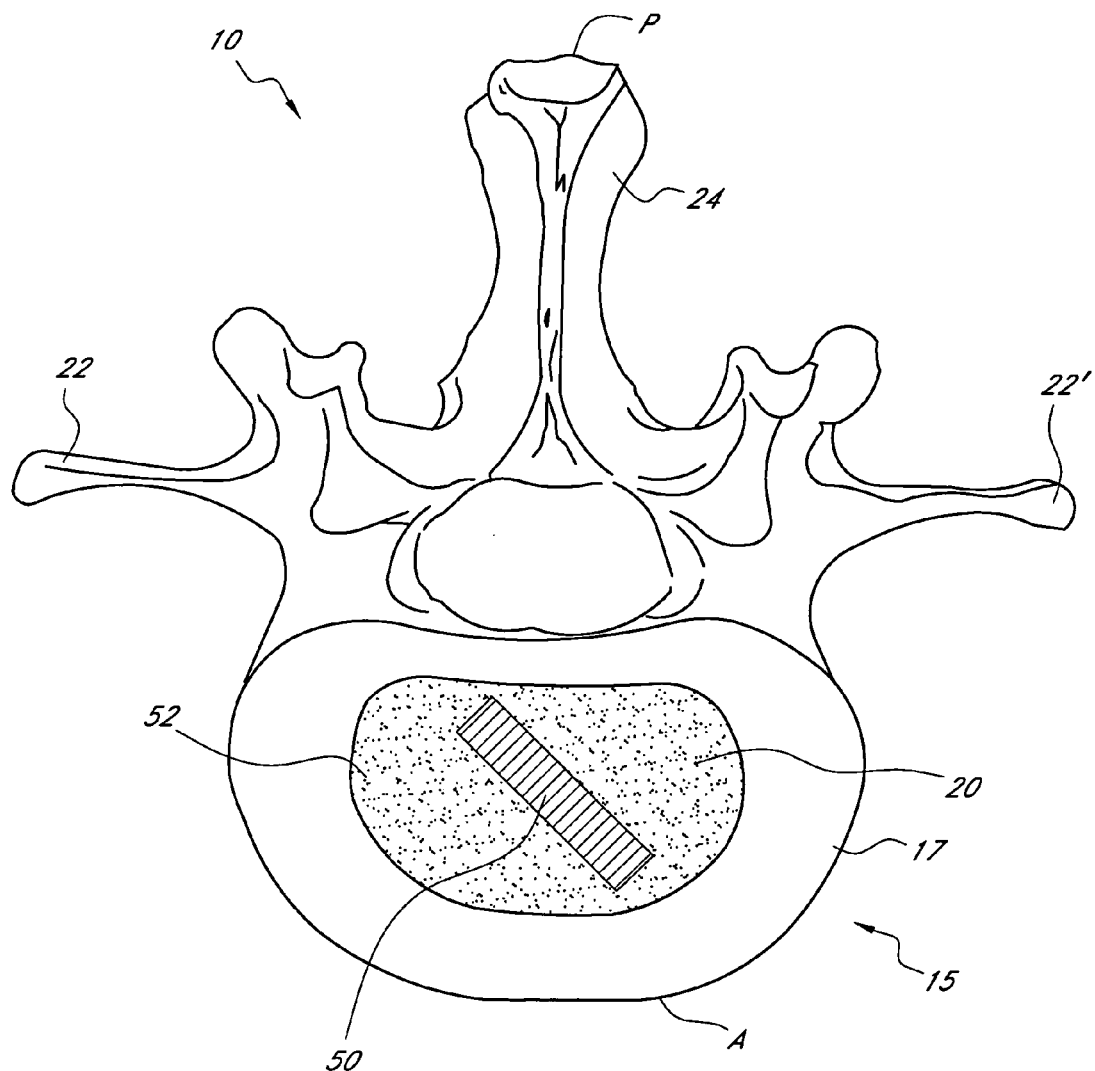
FIG. 1A is a cross-sectional view of a portion of a functional spine unit, in which part of a vertebra and vertebral disc are depicted.

Loss of vertebral disc tissue, such as NP, deflates the disc, causing a decrease in disc height. Significant decreases in disc height have been noted in up to 98% of operated patients. Loss of disc height increases loading on the facet joints, which may result in deterioration of facet cartilage and ultimately osteoarthritis and pain. As the joint space decreases, the neural foramina formed by the inferior and superior vertebral pedicles also close down which could lead to foraminal stenosis, pinching of the traversing nerve root, and recurring radicular pain. Loss of NP also increases loading on the remaining AF, and can produce pain. Finally, loss of NP results in greater bulging of the AF under load, which may result in renewed impingement by the AF on nerve structures posterior to the disc. Removal of NP may also be detrimental to the clinical outcome of disc repair.

Applicants own U.S. Pat. Nos. 6,425,919; 6,482,235; 6,508,839 and Published U.S. patent application Ser. No. 2002/0151979, each of which is hereby incorporated by reference in its entirety, and discloses, inter alia, methods and devices directed to reinforcing and augmenting the annulus of an vertebral disc. As will be explained, such devices and methods can be used with the inventions described herein.

In various aspects of the invention, a vertebral disc prosthesis, a method of implanting a prosthesis and a deployment device are disclosed.

In one aspect of the invention, the prosthesis is implanted into the interior region of the vertebral disc to move or displace, but not replace, the autologous or existing NP, AF or one or both endplates. The tissues of the AF, NP or endplate(s) is therefore displaced relative to the amount of prosthesis added. While a deminimis amount of vertebral tissue may be removed, a substantial amount of material (such as the NP) is not removed. In this manner, as will be explained, a more natural biomechanical state is achieved and functionality of the disc is retained. Prior methods include removal of some of the vertebral tissue, such as a substantial amount or all of the NP, which may disrupt the biomechanical function of the disc as well as the ability of the disc to survive. According to aspects of the present invention, the size or amount of prosthesis inserted into the interior region of the vertebral disc is a function of certain characteristics of the disc or the prosthesis. For example, the amount or size of prosthesis inserted into the disc may be dependent upon restoring the functionality of the disc (e.g., the ability of the disc to transfer nutrients or otherwise survive, the ability of the disc to carry the required loads and absorb stress or the reduction of pain). Restoring disc function may be determined by the resulting disc height desired, the resulting disc pressure desired or the resulting disc volume desired. The prosthesis may also be sized or positioned within the interior region of the vertebral disc such that it is spaced from at least one of the endplates of the vertebral disc. In this manner, the natural ability for the disc to transfer nutrients to and from the AF and the endplates by allowing a more natural diffusion of enriched fluids may be achieved. As will be explained in more detail below, in another aspect, the prosthesis may be formed of any suitable material as the present invention is not limited in this respect. In one embodiment, however, the prosthesis is formed of a material having a compression strength that is less than 4 $MN/m^2$. For example, a hydrogel material may be employed. As will be apparent to one of skill in the art, the hydrogel may be processed with suitable cross-linking agents or formed with a desired degree of cross-linking, or processed using a suitable freeze/thaw cycle to produce a material with the desired compressive strength.

In yet another aspect of the invention, to facilitate placement of the prosthesis within the vertebral disc, a deployment device is disclosed. The deployment device may include a number of features that, either singularly or in any suitable combination, enhance placement of the prosthesis. The deployment device may include at least one or more of the following: a depth stop to facilitate placement of the prosthesis relative to an anatomical feature; a curved or atriculatable end to facilitate inserting the prosthesis in a desired location; a plurality of openings formed on the insertion end of the device to allow a more uniform distribution of the prosthesis material within the disc; and a gauge to allow a determination as to whether a sufficient amount of the prosthesis material is placed within the vertebral disc. Further, rather than forcing the prosthesis into the interior region, the deployment device may be constructed such that upon retraction, the prosthesis is left behind.

The prosthesis may be shaped and sized or otherwise configured to be inserted through an opening in the vertebral disc. Such an opening may be a defect in the AF such as a hernia site, or may be a surgically created opening. The prosthesis may also be positioned within the interior region of the vertebral disc so as to be spaced away from the access opening and therefore reduce the likelihood that the prosthesis may be dispensed or extruded therefrom. Surgical approaches including transpsoas, presacral, transsacral, tranpedicular, translaminar, or anteriorly through the abdomen, may be used. The access opening can be located anywhere along the surface of the AF or even through the vertebral endplates.

Turning now to the figures, illustrative embodiments of the prosthesis and deployment device, and illustrative methods for inserting the prosthesis will now be described. Although certain features will be described with reference to a specific embodiment, the present invention is not limited in this respect, as any of the features described herein, and other suitable features, may be employed singularly or any suitable combination to form any suitable embodiment.

A functional spine unit includes the bony structures of two adjacent vertebrae (or vertebral bodies), the soft tissue (annulus fibrosis (AF), nucleus pulposus (NP), and endplates) of the vertebral disc, and the ligaments, musculature and connective tissue connected to the vertebrae. The vertebral disc is substantially situated in the vertebral space formed between the adjacent vertebrae.

Figure 1B:
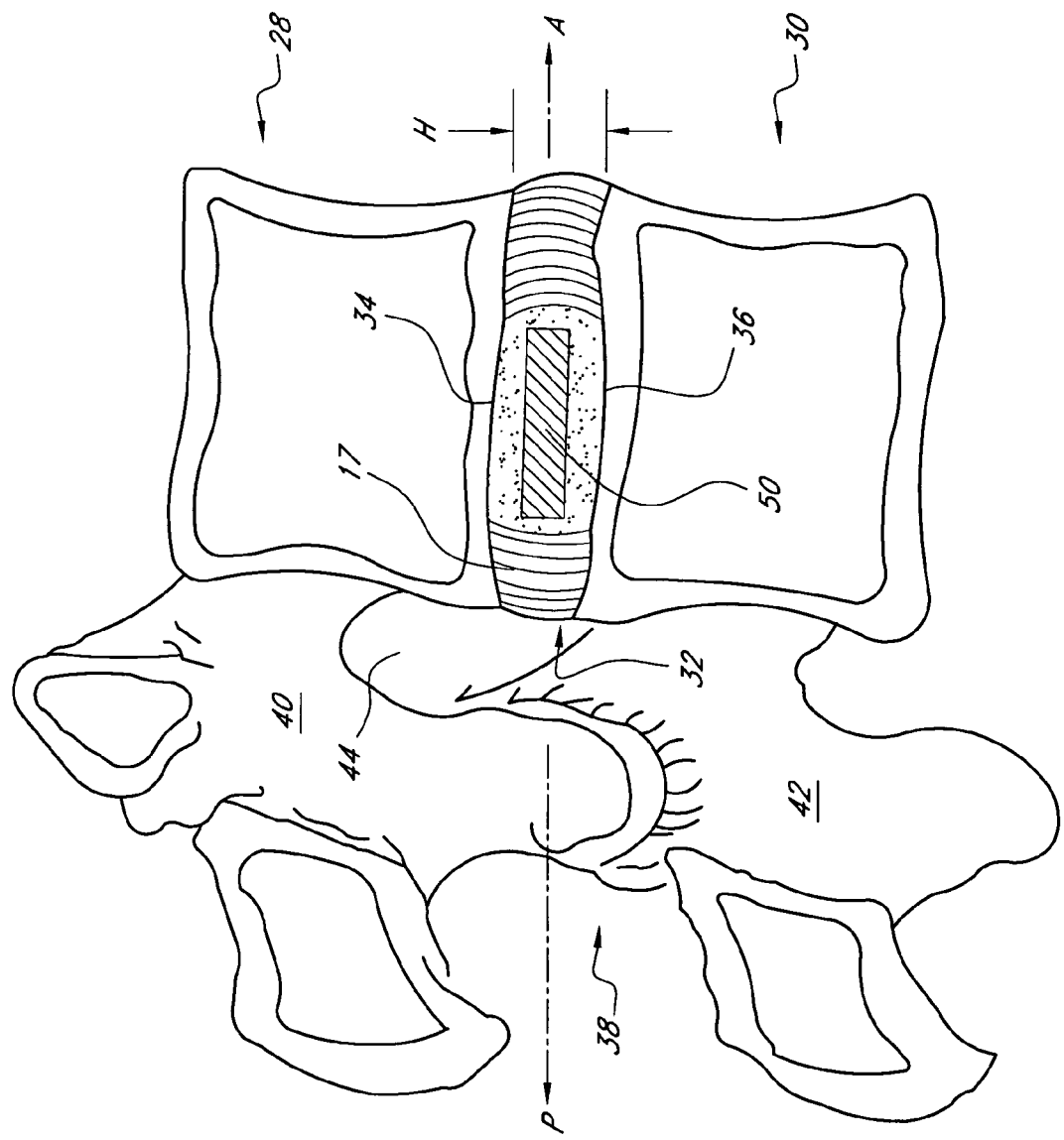
FIG. 1B is a side view of a portion of the functional spine unit shown in FIG. 1A, in which two lumbar vertebrae and the vertebral disc are visible, and wherein a prosthesis of the present invention is shown.

FIGS. 1A and 1B show the general anatomy of a functional spine unit 10. As used herein, the terms 'anterior' and 'posterior', 'superior' and 'inferior' are defined by their standard usage in anatomy, i.e., anterior is a direction toward the front (ventral) side of the body or organ, posterior is a direction toward the back (dorsal) side of the body or organ; superior is upward (toward the head) and inferior is lower (toward the feet).

FIG. 1A is a cross-sectional view of a vertebral body with the vertebral disc 15 superior to the vertebral body. Anterior (A) and posterior (P) sides of the functional spine unit are also shown. The vertebral disc 15 contains an annulus fibrosis (AF) 17 surrounding a central nucleus pulposus (NP) 20. Also shown in this figure are the left 22 and right 22' transverse spinous processes and the posterior spinous process 24.

FIG. 1B is a side view of two adjacent vertebral bodies 28 (superior) and 30 (inferior). Vertebral disc space 32 is formed between the two vertebral bodies and contains vertebral disc 15, which supports and cushions the vertebral bodies and permits movement of the two vertebral bodies with respect to each other and other adjacent functional spine units.

Vertebral disc 15 includes the AF 17, which normally surrounds and constrains the NP 20 to be wholly within the borders of the vertebral disc space. The vertebral disc 15 also includes superior endplate 34 and inferior endplate 36 that cooperate with the AF 17 to contain the NP 20 within the borders of the vertebral disc space. The vertebral bodies also include facet joints 38 and the superior 40 and inferior 42' pedicle that form the neural foramen 44. Loss of disc height (H) occurs when the superior vertebral body 28 moves inferiorly relative to the inferior vertebral body 30.

In one illustrative embodiment, the prosthesis 50 is inserted into the interior region 52 of the vertebral disc 15 so as to displace existing NP, AF or the endplate(s). That is, existing tissue, such as NP material, is not removed during insertion of the prosthesis, as is done in prior methods. As discussed above, prior methods include removal of some or all of the NP from the vertebral disc, which may disrupt the biomechanical function of the disc as well as the ability of the disc to survive. Also, prior prostheses were sized to merely fill the surgically created void within the interior region of the disc. Rather, according to aspects of the present invention, the prosthesis augments existing NP within the interior region of the vertebral disc rather than merely replace NP that was removed. In this manner, as will be explained, existing vertebral tissue may be displaced and a more natural biomechanical state is achieved, disc height is restored, and pain resulting from impingement by the AF on nerve structures, loading of facet joints or pinching of the transverse nerve root due to reduced joint space is minimized. A barrier may be employed to reduce the likelihood of the prosthesis escaping from the interior region. A barrier may also be employed to support the AF during and/or after the prosthesis is inserted.

In some instances, it may be desirable to monitor whether a sufficient amount of prosthesis or prosthesis material 50 is placed into the interior region 52 or whether the size of the prosthesis or prosthesis material 50 is sufficient to achieve the desired result, such as, for example, restoring the functionality of the disc. Thus, in one embodiment, certain disc characteristics are monitored during the implantation procedure. In one embodiment, disc height (H) is monitored such that the amount of prosthesis or prosthesis material 50 inserted into the disc 15 is a function of the desired height (H) of the disc 15. As explained above, restoring disc height may be beneficial in reducing pain.

As will become clear hereinafter, it is to be appreciated that the prosthesis or prosthesis material implanted into the interior region of the vertebral disc may have a predetermined geometry or may be initially in bulk form allowing a surgeon or other technician to insert a desired amount of the prosthesis or prosthesis material into the interior region of the disc. Thus, in embodiments where the prosthesis or prosthesis material is of a pre-formed geometry, the term "prosthesis" may be used. In embodiments where the prosthesis or prosthesis material is a portion of a bulk material (such as when the prosthesis or prosthesis material is formed from a liquid or fluid material) the phrase "prosthesis material" may be used. In both embodiments, however, reference numeral "50" is used. Nevertheless, the present invention is not limited in this respect, as the tern "prosthesis" may be used to refer to a portion of a bulk material and the term "prosthesis material" may be used to refer to a pre-formed geometry. As such, the term "prosthesis" is used herein to generically refer to either embodiment.

Determining the height (H) may be performed using any suitable means or method, as the present invention is not limited in this respect. In one embodiment, a caliper or other measuring device to determine the disc height may be used. Alternatively, disc height may be monitored using any suitable imaging system, such as MRI, X-ray or CT Scan, as the present invention is not limited in this respect. Further, such height data may be obtained either during the procedure or post-operatively by, for example, comparing pre- and post-operative disc heights. Once the desired disc height (H) is achieved, continued insertion of the prosthesis 50 into the interior region is terminated. The desired disc height (H) may be determined on a case by case basis. In one embodiment, the disc height (H) may be increased by an amount ranging between approximately 1 mm and approximately 10 min. Other suitable ranges include 0.1 mm-5 mm and 5 mm-10 mm or even a narrower range, such as 0.1 mm-3 mm, 3 mm-6 mm and 6 mm-9 mm. It should be appreciated that the present invention is not limited to any particular resulting disc height (H), as other final disc heights or ranges may be desired.

According to one aspect of the invention, increasing disc pressure may be desirable to restore natural disc function. However, care should be taken so as not to exceed pressure limits of the disc. Studies have shown that pressures exceeding much more than 6 atmospheres may damage the endplates of the vertebral disc. Therefore, instead of or in addition to monitoring the disc height, the pressure within disc 15 may be monitored. That is, the amount of prosthesis material 50 inserted or the size of the prosthesis itself may be a function of an increase in disc pressure. In one embodiment, the amount of prosthesis implanted results in an increase in pressure ranging from approximately 0.1 atmospheres to approximately 5 atmospheres. It should be appreciated however that the present invention is not limited in this respect and that other suitable pressure ranges may be desirable. For example, pressure increases ranging from 0.1-2 atmospheres, 2-4 atmospheres or even 4-6 atmospheres may be achieved.

Typically, the disc pressure is intradiscal pressure and the pressure is monitored while the disc 15 is in a resting state, e.g., when there is no substantial axial force on the disc 15.

The disc pressure may be monitored using any suitable technique, as the present invention is not limited in this respect. As will be described in greater detail, the actual pressure within the interior region of the disc may be monitored or it may be measured indirectly by measuring the force required to insert the prosthesis 50. That is, as the prosthesis 50 is inserted into the interior region 52, the force resisting the insertion may increase. Measuring or monitoring this resistance force may indicate the internal pressure within the disc 15.

According to one aspect of the invention, increasing disc volume may be desirable to restore natural disc function. Also, increasing disc volume may be employed as a method of indirectly increasing disc pressure or disc height. Thus, in another illustrative embodiment, the volume of the disc 15 may be monitored. Monitoring this characteristic may be employed in combination with monitoring the disc pressure and/or monitoring the disc height. Monitoring the disc volume may be achieved by CT scanning, X-ray imaging or MRI as the present invention is not limited in this respect. Also, such monitoring may be performed by comparing pre- and post-operative disc volumes.

Alternatively, the volume of prosthesis material 50 being inserted into the interior region 52 may be measured directly by monitoring the amount or size of the prosthesis itself. It should be appreciated that the present invention is not limited in this respect, as other suitable methods of monitoring disc or prosthesis volume may be employed. The volume of the prosthesis material may also be adjusted to compensate for extra swelling due to, for example, any existing herniations in the AF 17. For example, the volume of the prosthesis material 50 inserted into the interior region 52 may be increased to accommodate such swelling.

A direct measurement of the amount of prosthesis material being inserted may be employed, such as by the use of a metered dispensing implement. Alternatively, because the volume of the prosthesis material is a function of the specific dimensions of the vertebral disc, the prosthesis volume may be gathered from CT scan data, MRI data or other similar data from another imaging protocol. Thus, for example, prostheses with lesser volume can be used with smaller discs and those with limited herniation and those that otherwise require less NP displacement to increase disc height or intradiscal pressure.

In one illustrative embodiment, the volume of prosthesis material 50 inserted into the interior region of the vertebral disc may range between approximately 0.1 ml and approximately 6 ml. Other suitable volume ranges, such as between approximately 0.1 ml and approximately 2 ml or between approximately 0.5 ml to approximately 2 ml, may be employed, as the present invention is not limited in this respect. The amount of prosthesis material 50 implanted depends upon a number of factors, including the amount of vertebral tissue, such as NP, lost through any herniation or degeneration and any increase in stiffness vertebral tissue, such as NP, as it is displaced with the prosthesis material. Further, the amount of prosthesis material inserted may depend upon the resulting augmentation volume of the vertebral disc desired.

Figure 2:
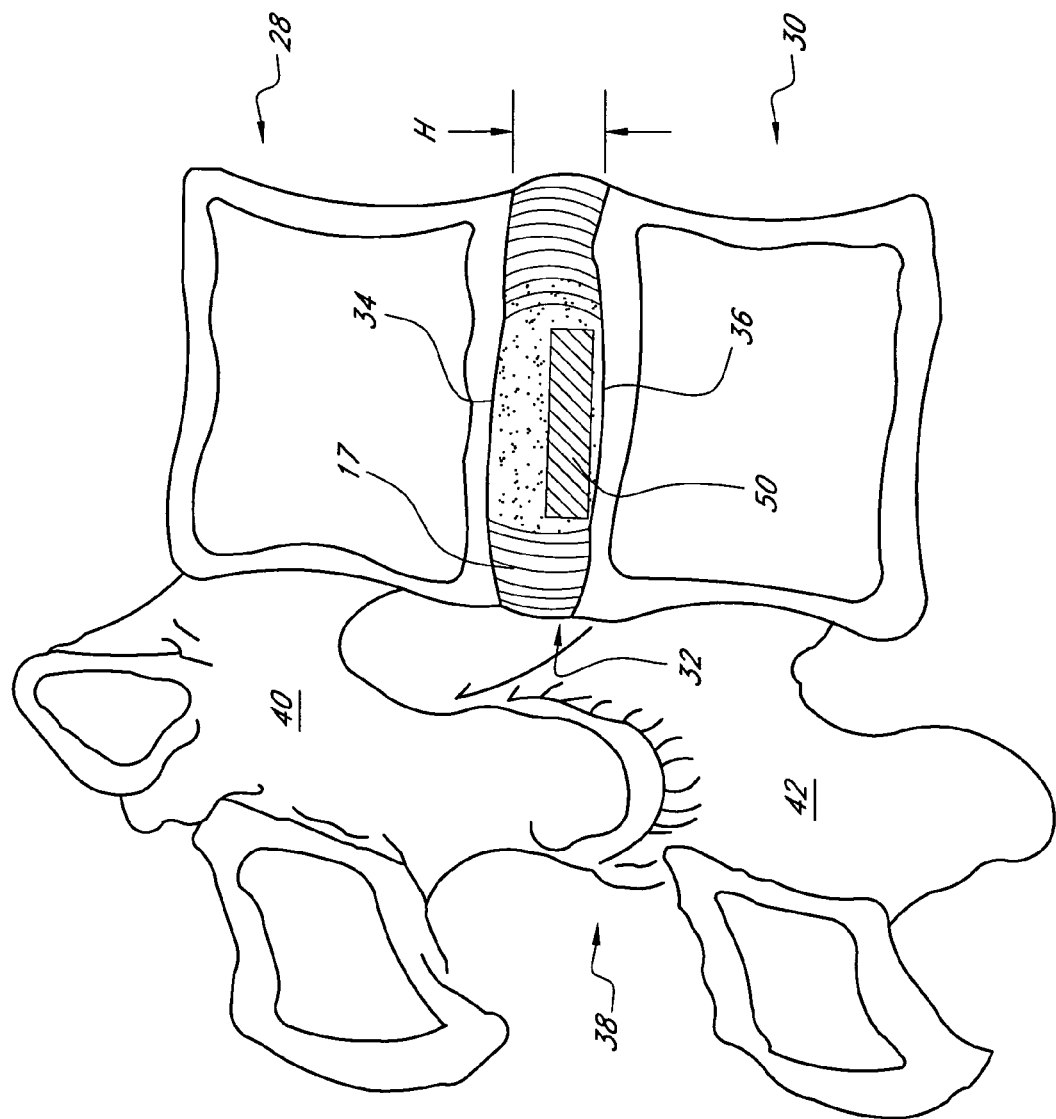
FIG. 2 is a side view of the functional spine unit shown in FIG. 1A, wherein a prosthesis according to another aspect to the invention is shown.

Typical failure modes with existing vertebral disc implants may be caused by placing the implant directly between two opposing endplates where the implant functions to resist compression. In this respect, the mechanical properties of the prosthesis may create a stress concentration along the endplates and fracturing of the endplates may occur. Furthermore, placing the prosthesis against both endplates may interfere with fluid and nutrient transfer in and out of the vertebral disc. Thus, in one illustrative embodiment, as shown in FIGS. 1A and 1B, the prosthesis 50 is sized and shaped so as not to occupy the entire volume of the interior region 52 of the vertebral disc. In another embodiment, as shown in FIG. 2, the prosthesis 50 is sized and positioned within the interior region so as to be spaced from at least one endplate 34. In another embodiment, the prosthesis 50 is sized so as to be spaced from both endplates 34, 36. In this manner, the prosthesis 50 may be partially or wholly surrounded by NP material.

Upon insertion of the prosthesis 50 into the vertebral disc 15, displacement of the vertebral tissue occurs, such that the vertebral tissue is pushed and expands radially. For example, when the prosthesis displaces NP, the NP moves in opposite directions, i.e., towards the endplates 34, 36. The NP 20 cushions the prosthesis 50 and at least one of the endplates 34, 36, and preferably both endplates, and allows for a more natural diffusion of fluids and nutrients. In the above embodiments, the prosthesis 50 is surrounded by NP; however, it need not be. For example, in another embodiment, the prosthesis 50 is placed so as to lie adjacent the AF 17, as shown in FIG. 2.

Figure 3A:
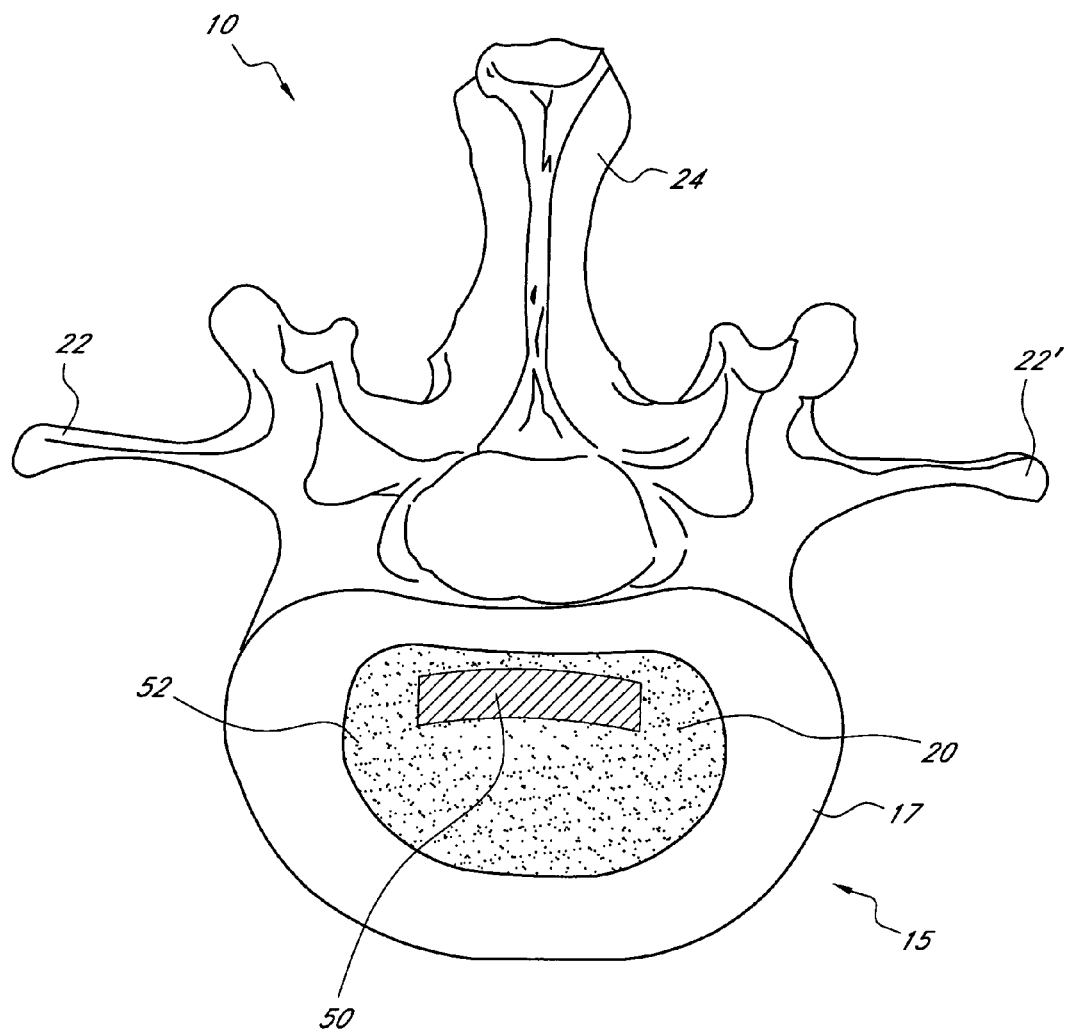
FIGS. 3A and 3B are views of the vertebral disc, wherein a prosthesis according to yet another aspect of the invention is shown.
Figure 3B:
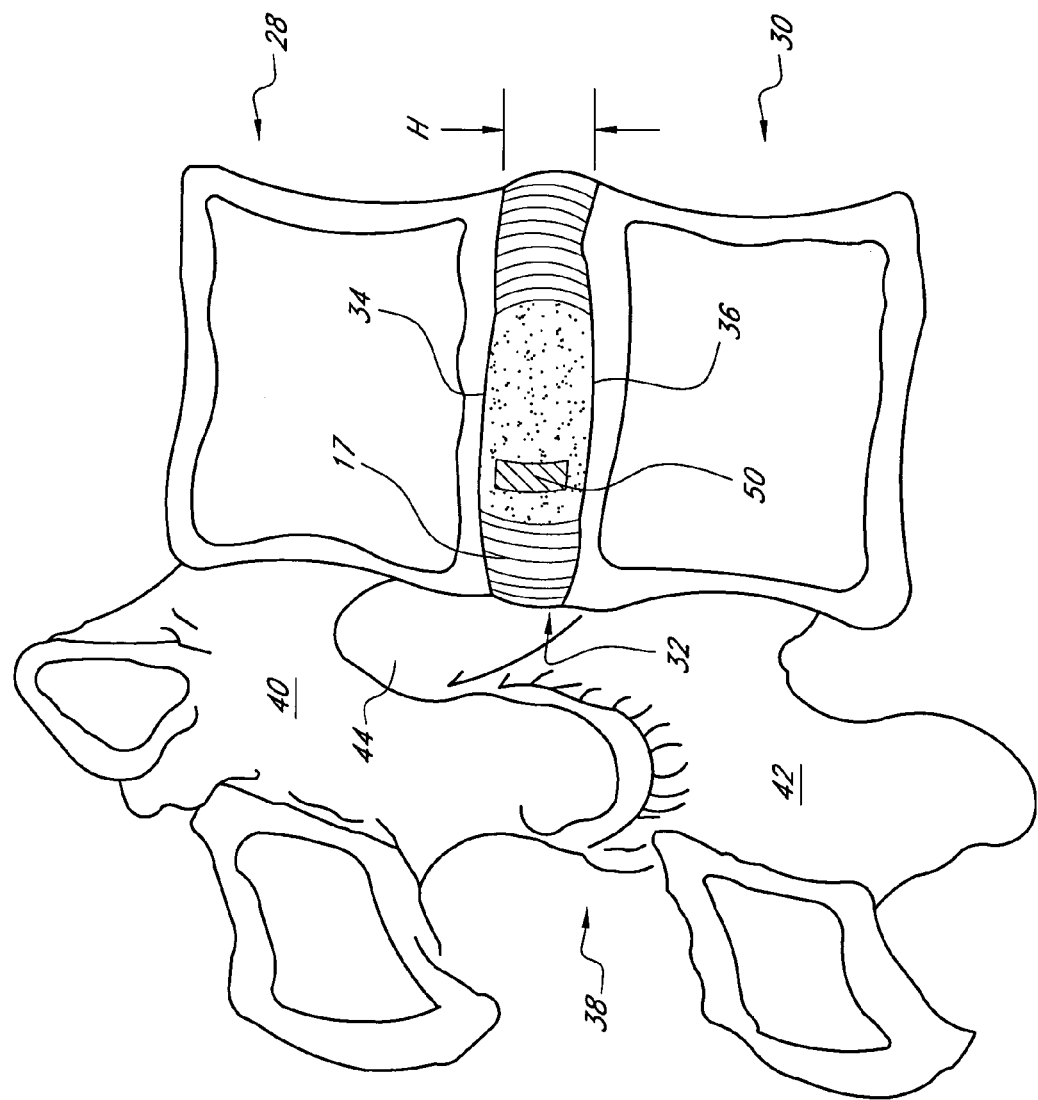

The position of the prosthesis within the interior region of the vertebral disc may also be selected so as to alter the axis of rotation or reaction forces acting on a given functional spinal unit. A functional spinal unit moves with an axis of rotation that dictates which part of the functional spinal unit experiences the most motion or loading. The reaction force of the vertebral disc controls the axis of rotation, therefore altering the reaction force location changes the axis of rotation to reduce relative motion of parts of a functional spinal unit. For example, as shown in FIGS. 3A and 3B, adding the prosthesis 50 to the posterior of vertebral disc 15 shifts the axis of rotation closer to the facets 38, thereby reducing facet loading and facet pain. Furthermore, positioning the prosthesis posteriorly has the effect of increasing the disc height near the facets, which could also have the effect of reducing and relieving pain.

Figure 4:
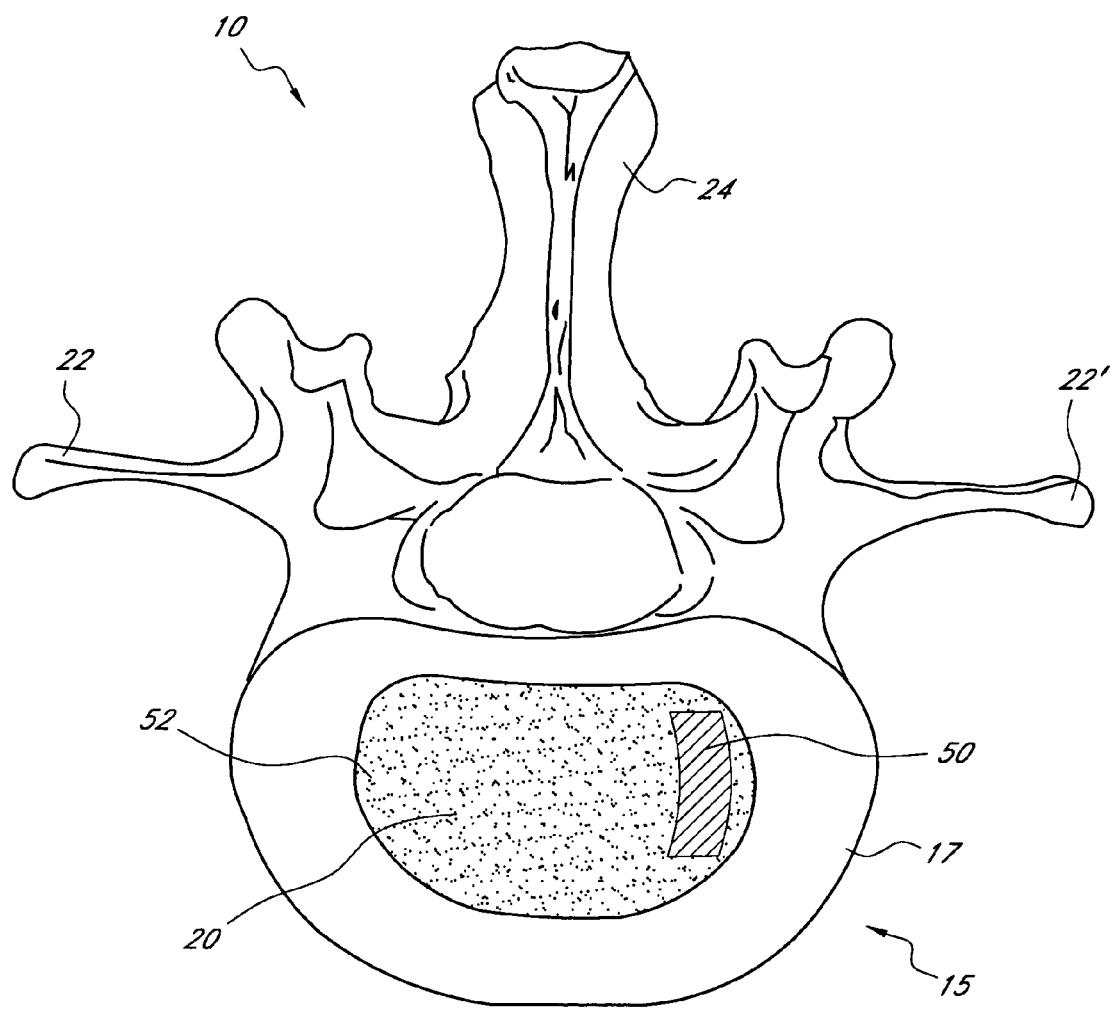
FIG. 4 is a cross-sectional view of a portion of a functional spine unit, wherein a prosthesis according to still another aspect of the invention is shown.
Figure 5:
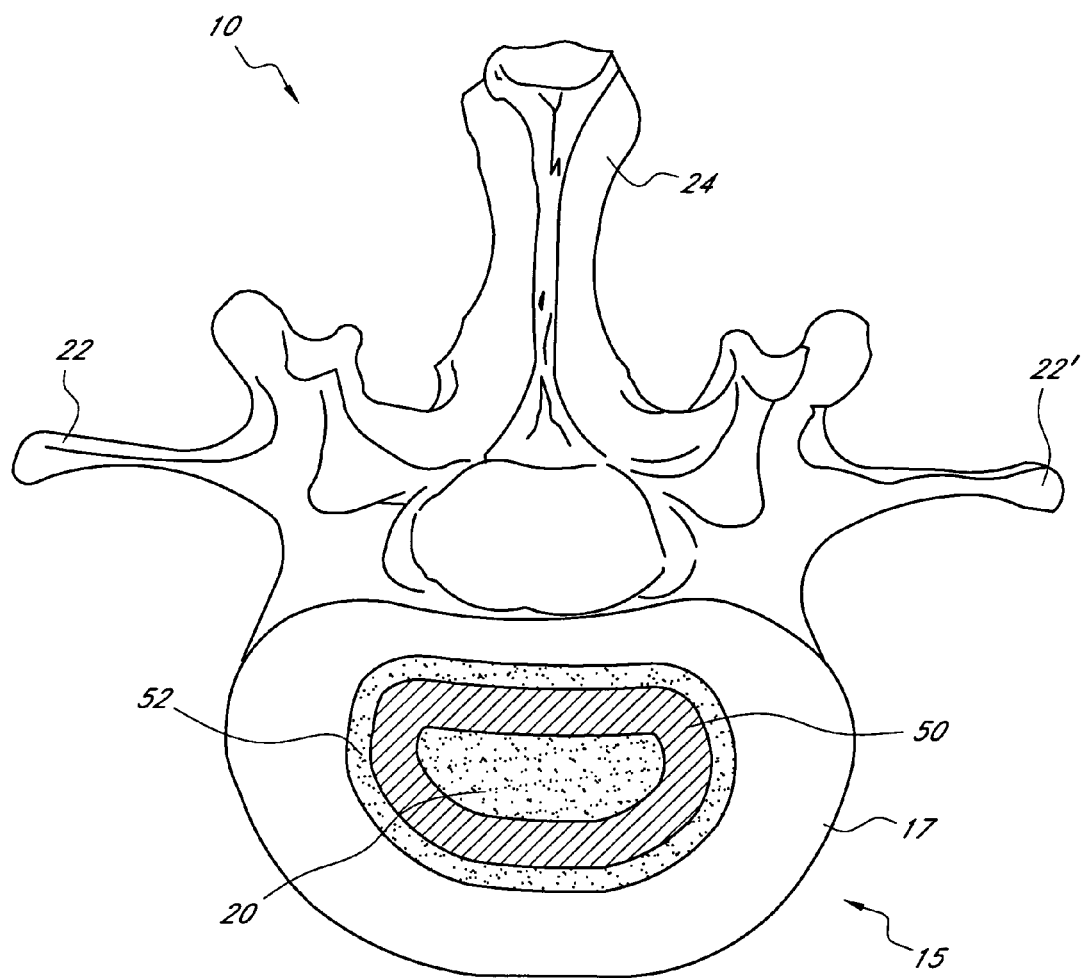
FIG. 5 is a cross-sectional view of a portion of a functional spine unit, wherein a prosthesis according to yet another aspect of the invention is shown.

Other suitable positions for the prosthesis also may be employed. For example, as shown in FIG. 4, the prosthesis 50 may be positioned on one side of the vertebral disc 15 to restore symmetrical lateral height and bending that may have been altered by disc degeneration or an AF defect. A circumferential prosthesis 50, as shown in FIG. 5, or multiple prosthesis positioned about the circumference of the inner region (not shown) may also be employed. Other suitable combinations of positions for the prosthesis also may be employed to achieve other desired results.

Figure 6A:
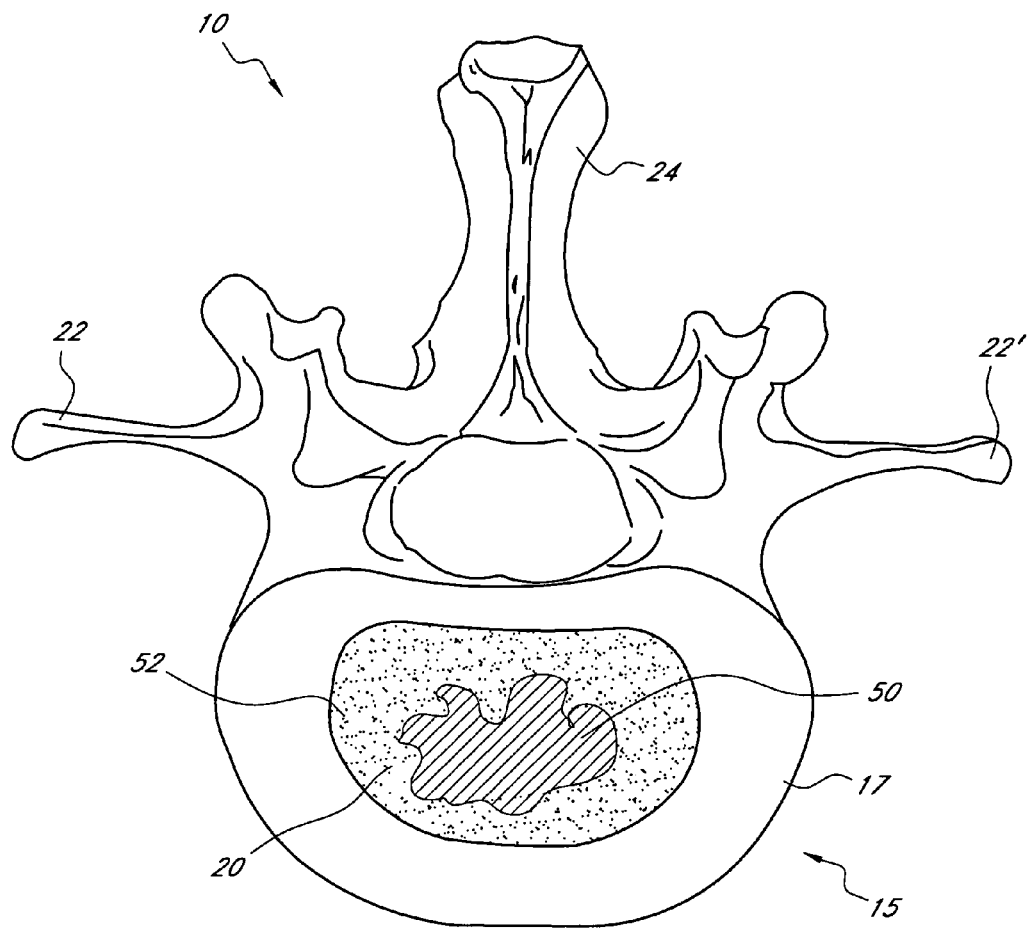
FIGS. 6A and 6B are views of a portion of a functional spine unit, wherein a prosthesis according to yet another aspect of the invention is shown.
Figure 6B:
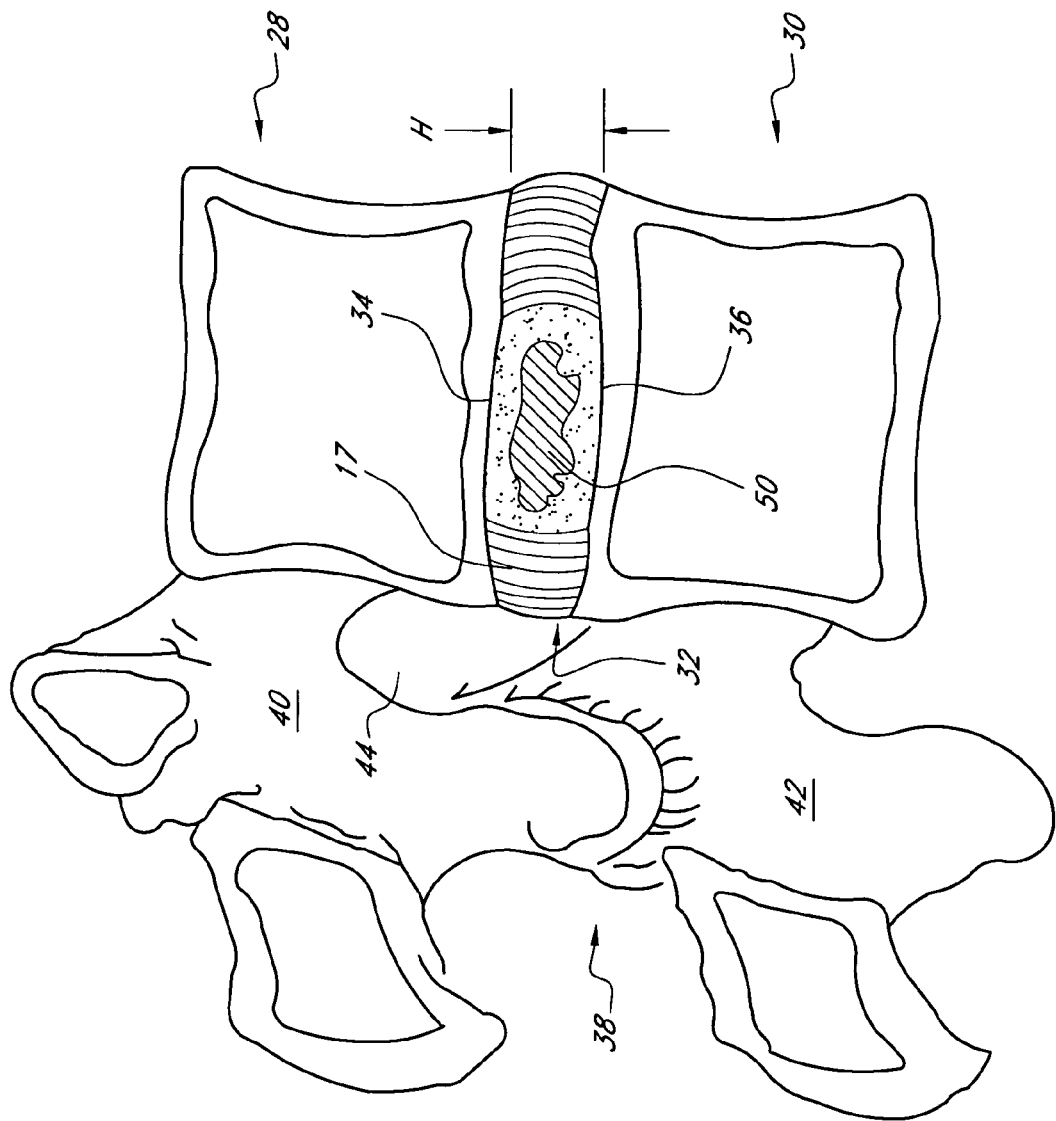
Figure 8:
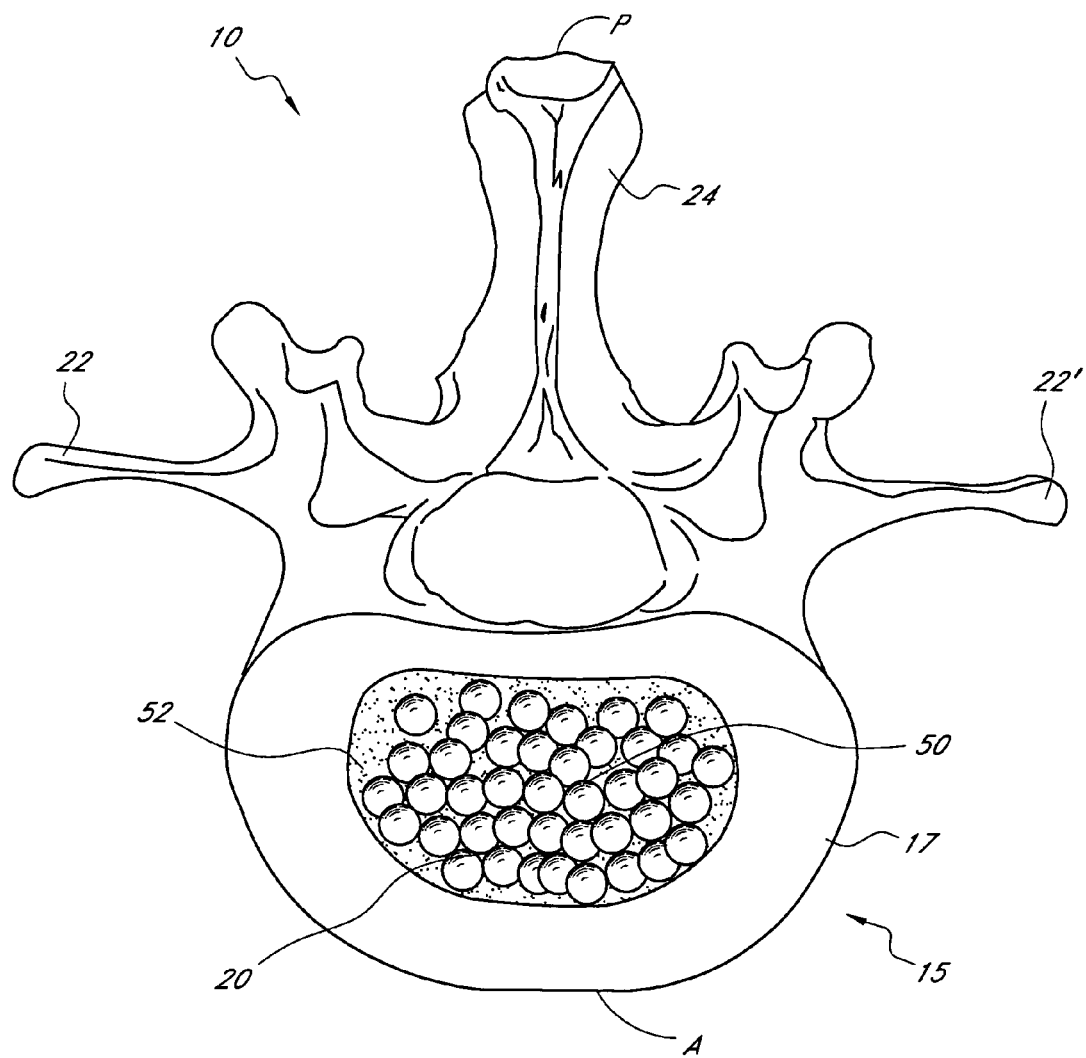
FIG. 8 is a cross-sectional view of a portion of a functional spine unit, wherein a prosthesis according to still another aspect of the invention is shown.
Figure 9:
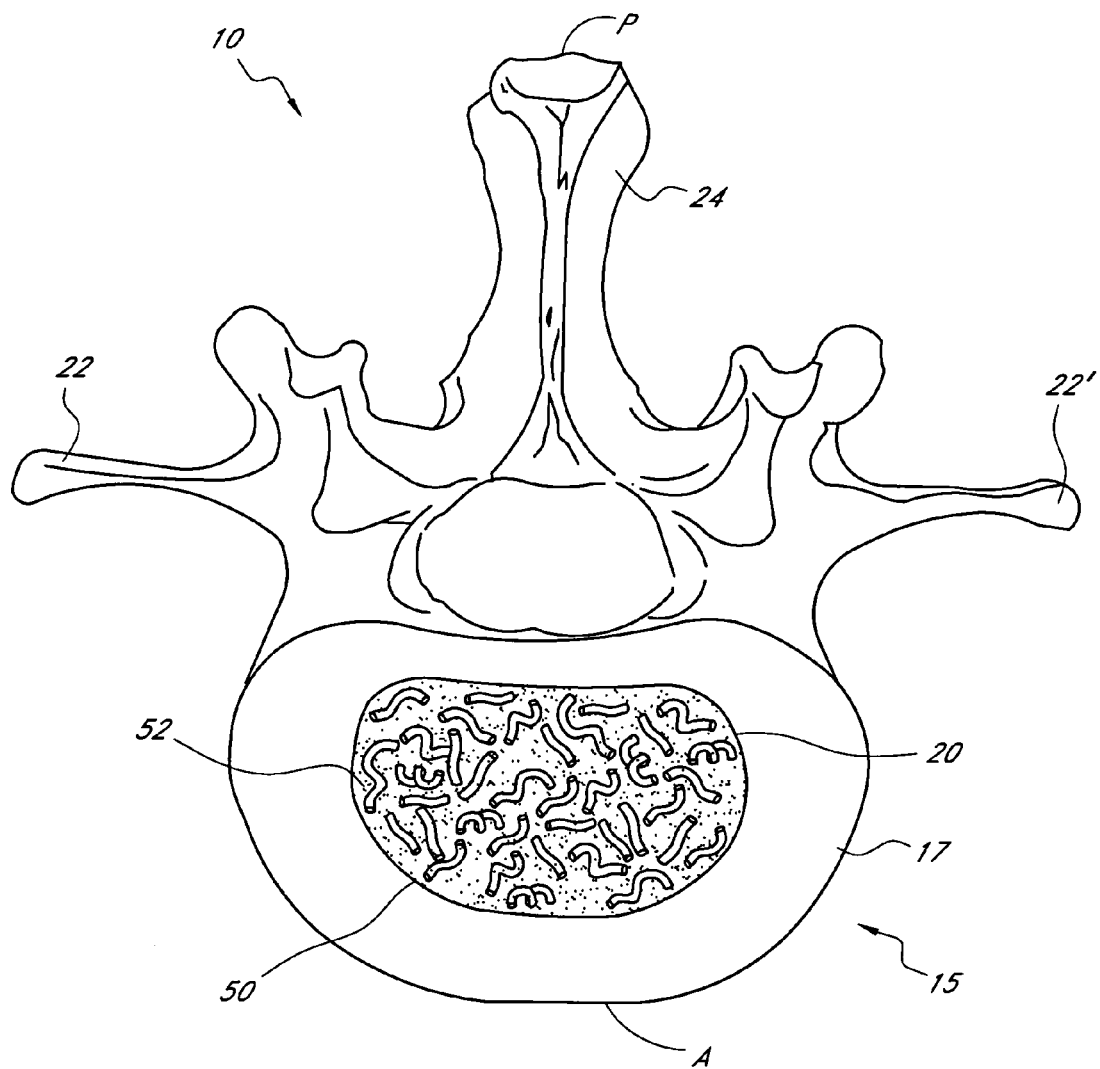
FIG. 9 is a cross-sectional view of a portion of a functional spine unit, wherein a prosthesis according to still another aspect of the invention is shown.

Prosthesis 50 can be formed into any suitable shape. Prosthesis 50 may be cube-like, spherical, disc-like, ellipsoid, rhombohedral, cylindrical, kidney, wedge, planar, or amorphous in shape as shown in FIGS. 6A and 6B. Further, a single prosthesis or prosthesis formed from multiple sections or separate pieces may be employed. A plurality of prostheses also may be employed and may be formed as beads, as shown in FIG. 8, substantially straight and/or spiral rods, as shown in FIG. 9, geometric solids, irregular solids, sheets or any other suitable shape disclosed herein or otherwise formed. Of course, any suitable combination of the above mentioned or other shapes may be employed.

Figure 7A:
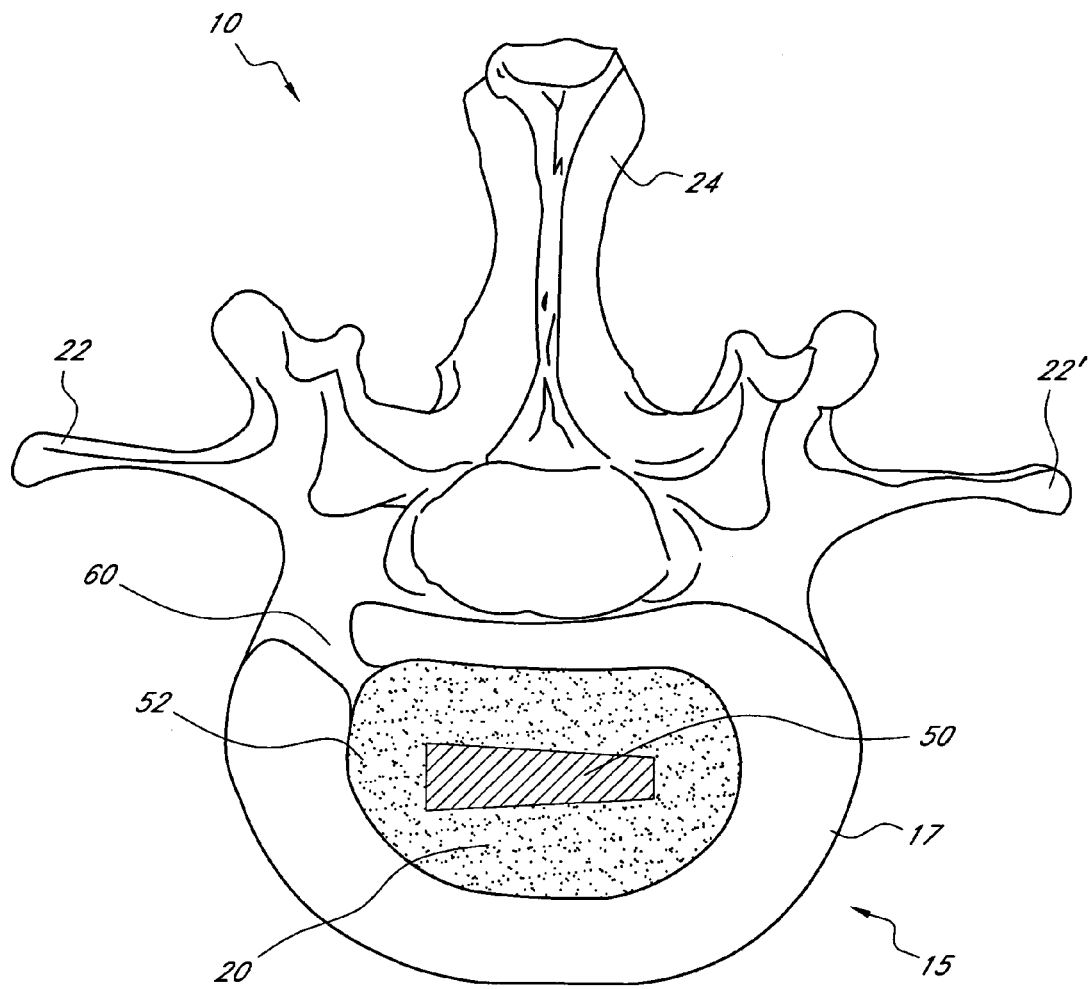
FIGS. 7A and 7B are views of a functional spine unit, wherein a prosthesis according to yet another aspect of the invention is shown.
Figure 7B:
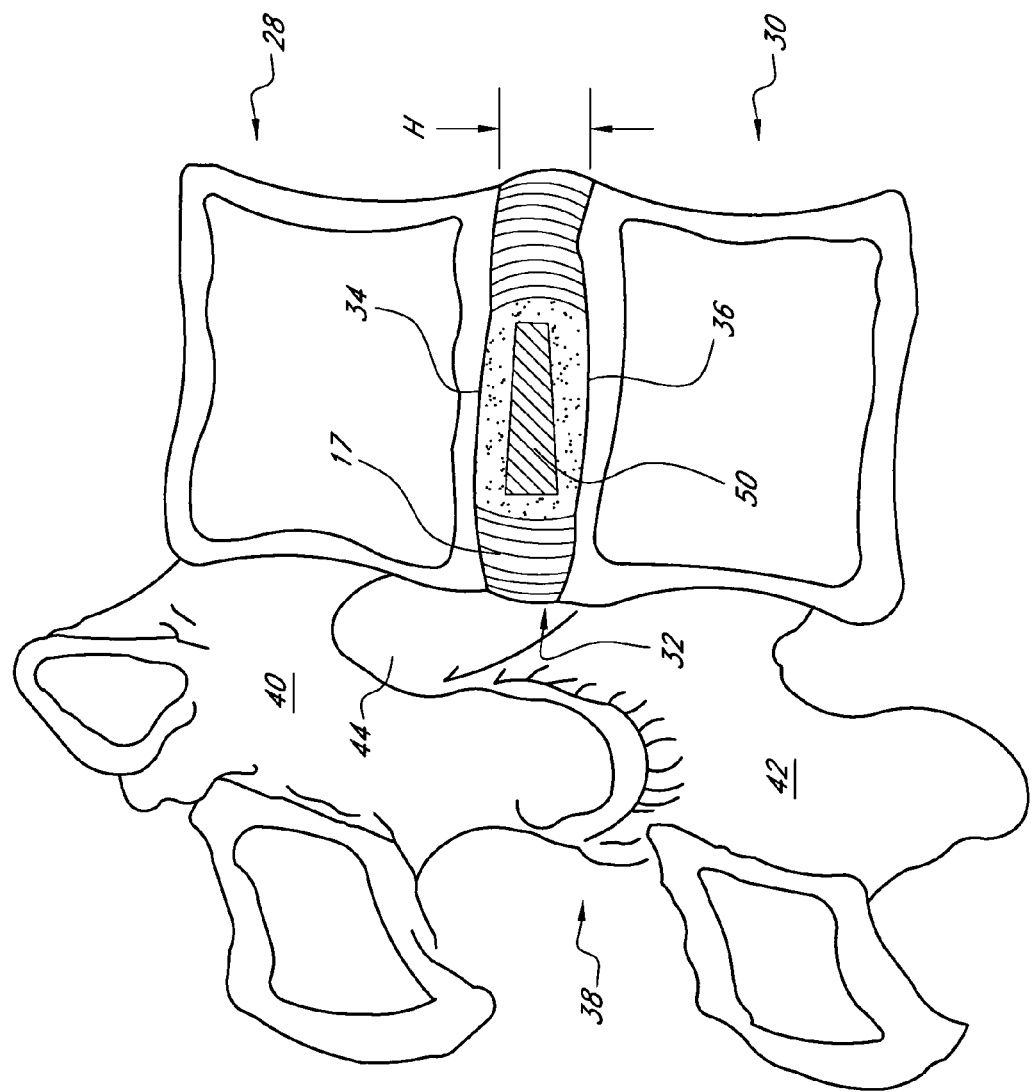

In another embodiment, the prosthesis 50 is shaped to resist being extruded from the interior region of the vertebral disc 15. In one example, as shown in the illustrative embodiment of FIGS. 7A and 7B, the prosthesis 50 is sized to be larger than the access opening 60 formed in the vertebral disc 15 for inserting the prosthesis 50. Alternatively, or in addition, the prosthesis may be formed as a wedge, as shown, with the larger end of the wedge facing the opening 60 such that any force tending to push the wedge out the access opening would cause the prosthesis to occlude the access opening 60. Of course, the prosthesis may be shaped such that any axial loads on the prosthesis would tend to cause the prosthesis to move away from the access opening. For example, a wedge-shaped prosthesis with the smaller end facing the opening 60 may respond to axial loads by tending to move away from the opening.

To aid in healing of the disc or otherwise provide therapy, the prosthesis may be impregnated, coated or otherwise deliver various therapeutic agents, such as drugs, time-release drugs, genetic vectors, naked genes or the like to renew growth, reduce pain, aid healing, or reduce infection.

The prosthesis may be formed of any suitable material, as the present invention is not limited in this respect. The prosthesis may be formed as a fluid (e.g., liquid or gas), a solid, a gel, a semi-solid, or any suitable combination thereof. Exemplary fluid prostheses or prosthesis materials include, but are not limited to, various pharmaceuticals (steroids, antibiotics, tissue necrosis factor alpha or its antagonists, analgesics); growth factors, genes or gene vectors in solution; biologic materials (hyaluronic acid, non-crosslinked collagen, fibrin, liquid fat or oils); synthetic polymers (polyethylene glycol, liquid silicones, synthetic oils); and saline.

In one illustrative embodiment, the prosthesis 50 is formed of a biocompatible material. Examples include biocompatible viscoelastic materials such as hydrophilic polymers, hydrogels, homopolymer hydrogels, copolymer hydrogels, multi-polymer hydrogels, or interpenetrating hydrogels, acrylonitrile, acrylic acid, acrylimide, acrylimidine, including but not limited to PVA, PVP, PHEMA, PNVP, polyacrylamides, poly(ethylene oxide), polyvinyl alcohol, polyarylonitrile, and polyvinyl pyrrolidone, or combinations thereof. It is preferred, but not required, that such materials may exhibit mechanical properties, swelling pressures and/or diffusion capabilities similar to the natural NP in order to supplement the NP without causing undo stress concentrations.

In other embodiments, the prosthesis 50 may be formed from solid material, such as woven or non-woven materials or may include minute particles or even powder. The prosthesis 50 also may be porous or semi-porous. Candidate materials include, but are not limited to: metals, such as titanium, stainless steels, nitinol, cobalt chrome; resorbable or non-resorbing synthetic polymers, such as polyurethane, polyester, PEEK, PET, FEP, PTFE, ePTFE, Teflon, PMMA, nylon, carbon fiber, Delrin, polyvinyl alcohol gels, polyglycolic acid, polyethylene glycol; elastin; fibrin; ceramics, silicone, gel or rubber, vulcanized rubber or other elastomers; gas filled vesicles, biologic materials such as morselized or block bone, hydroxy apetite, collagen or cross-linked collagen, muscle tissue, fat, cellulose, keratin, cartilage, protein polymers, transplanted or bioengineered materials; various pharmacologically active agents in solid form; or any combination thereof. The solid or gel prosthesis materials may be rigid, wholly or partially flexible, elastic or viscoelastic in nature. The prosthesis material may be hydrophilic or hydrophobic. Hydrophilic materials, mimicking the physiology of the NP, may be delivered into the disc in a hydrated or dehydrated state. Biologic materials may be autologous, allograft, zenograft, or bioengineered. Where rigid materials are employed, the prosthesis may be shaped as small particles, powders, balls or spheres.

In some embodiments of the present invention, a multiphase system may be employed; for example, a combination of solids, fluids or gels may be used. Such materials may create primary and secondary levels of flexibility within an vertebral disc space. Thus, in use, the spine will flex easily at first as the vertebral disc pressure increases and the fluid flows, loading the annulus. Then, as the disc height decreases flexibility may decrease. This combination may also prevent damage to the AF under excessive loading as the prosthesis may be designed to resist further compression such that further pressure on the AF is limited.

Any of a variety of additional additives such as thickening agents, carriers, polymerization initiators or inhibitors may also be included, depending upon the desired infusion and long-term performance characteristics. In general, "fluid" is used herein to include any material which is sufficiently flowable at least during the infusion (i.e., implantation) process, to be infused by a delivery device into the interior region of the vertebral disc. The prosthesis material may remain "fluid" after the infusion step, or may polymerize, cure, or otherwise harden to a less flowable or nonflowable state.

In one embodiment, in situ polymerizing prosthesis materials that are well-known in the art and are described in U.S. Pat. No. 6,187,048, incorporated herein by reference, may be used. Phase changing augmentation preferably changes from a liquid to a solid or gel. Such materials may change phases in response to contact with air, increases or decreases in temperature, contact with biologic liquids or by the mixture of separate reactive constituents. These materials may be delivered through an opening in the AF or down a tube or cannula placed percutaneously into the disc. Once the materials have solidified or gelled, they may exhibit the previously described characteristics of a solid prosthesis material.

Additional additives and components of the prosthesis material are recited below. In general, the nature of the material may remain constant during the deployment and post-deployment stages or may change, from a first infusion state to a second, subsequent implanted state. For example, any of a variety of materials may desirably be infused using a carrier such as a solvent or fluid medium with a dispersion therein. The solvent or liquid carrier may be absorbed by the body or otherwise dissipate from the disc space post-implantation, leaving the material behind. For example, any of a variety of the powders identified below may be carried using a fluid carrier. In addition, hydrogels or other materials may be implanted or deployed while in solution, with the solvent dissipating post-deployment to leave the hydrogel or other media behind. In this type of application, as discussed above, the disc space may be filled under higher than ultimately desired pressure, taking into account the absorption of a carrier volume.

In one embodiment, the prosthesis material comprises a material having a compressive strength that is less than approximately 4 $MN/m^2$. In another embodiment, the prosthesis material has a compressive strength of approximately 2.5 $MN/m^2$ to approximately 3.5 $MN/m^2$. Other suitable prosthesis materials having compressive strengths less than or equal to approximately 2.5 $MN/m^2$ or approximately 3.5 $MN/m^2$ to approximately 4 $MN/m^2$ may be employed.

In addition, the prosthesis material may have a Poisson's ratio that is between approximately 0.30 and approximately 0.49. Such a Poisson's ratio may be employed to effectively distribute the load outward toward the AF. In one embodiment, the Poisson's ratio is between a range of approximately 0.35 and approximately 0.49. Rubber and polymeric materials may be used or otherwise formed to produce the desired Poisson ratio. In one embodiment, a hydrogel, such as PVA, PGA or PMMA, may be used.

As discussed above, it may be desirable to provide a prosthesis material that mimics as closely as possible the NP within the interior region of the vertebral disc. Thus, the prosthesis may be formed of a material that absorbs and/or releases fluids within a certain period of time and under certain conditions similar to the absorption and release of fluids from the natural NP. Upon high axial loads of the vertebral disc, the prosthesis may release fluids to help diffuse shock loading. Similarly, the ability for the prosthesis to absorb fluid should be sufficiently rapid so as to rebulk when fluid is otherwise released from the prosthesis. In one embodiment, it may be desirable for the prosthesis to absorb fluids during a 5 to 10 hour sleep cycle so as to restore any fluid loss during the day. In one embodiment, the prosthesis is formed of a material that may enable it to absorb approximately 50% to 100% of its volume. However, the present invention is not limited in this respect and other suitable prosthesis materials or characteristics of a prosthesis material may be employed to achieve other rehydration volumes. Rubber and polymeric materials may be used. In one embodiment, a hydrogel, such as PVA, PGA or PMMA, may be used.

In one embodiment, the prosthesis material has a swelling pressure between approximately 0.1 $MN/m^2$ and approximately 9 $MN/m^2$ for given volume range between approximately 0.1 mL and 6.0 mL. This may have the advantage of allowing a smaller prosthesis to swell and fit into the irregularities within the natural NP until equilibrium pressure is achieved. Rubber and polymeric materials may be used. In one embodiment, a hydrogel, such as PVA, PGA or PMMA, may be used.

In one embodiment, the prosthesis material may be formed as a hydrogel having a compressive strength ranging between approximately 2.5 $MN/m^2$ and approximately 3.5 $MN/m^2$. In addition, the prosthesis material may preferably have a swelling characteristics that enables it to rehydrate approximately 50% to 100% of its volume within a 1 hour to 8 hour time period under a compressive stress ranging from approximately 0.2 $MN/m^2$ and approximately 0.8 $MN/m^2$. Further, the prosthesis material may hydrate in less time when in an unloaded or unconstrained environment. Further, in this embodiment, the prosthesis material may have a Poisson's ratio ranging from approximately 0.35 to approximately 0.49 under a compressive stress ranging from approximately 0.5 $MN/m^2$ to approximately 2 $MN/m^2$. Rubber and polymeric materials may be used. In one embodiment, a hydrogel, such as PVA, PGA or PMMA, may be used.

In some embodiments it may be desirable to provide a more uniform loading at the junction between the prosthesis material and the NP, AF or endplates to reduce stress concentration and limit damage to any of the foregoing. Thus, in one embodiment, the prosthesis material may be a relatively soft and flexible material. In addition, in one embodiment, the prosthesis material may be isotropic. Rubber and polymeric materials may be used. In one embodiment, a hydrogel, such as PVA, PGA or PMMA, may be used.

In one embodiment, the prosthesis is a biocompatible isotropic hydrogel, such as PVA, PGA or PMMA, having a compressive strength of less than 4 $MN/m^2$.

In some instances it may be desirable to remove the prosthesis material from the interior region of the vertebral disc. Thus, in one embodiment, the prosthesis is sized, shaped or otherwise configured so as to be relatively easily removed after having been implanted. In one embodiment, this result may be achieved by selecting the shape of the prosthesis and/or the rigidity or deformability of the material.

The prosthesis implanted into the interior region of the disc may also be used in conjunction with a barrier that blocks, covers or otherwise occludes the access opening, whether it be surgically created or a hernia site. After the prosthesis 50 is inserted into the interior region, a barrier 70 (see FIG. 10), such as that disclosed in applicants commonly assigned patents and patent application, including U.S. application Ser. No. 10/055,504, U.S. Pat. Nos. 6,425,919 and 6,508,839, each of which is hereby incorporated by reference, is inserted. Of course, other suitable barriers or no barrier may be employed.

Figure 10:
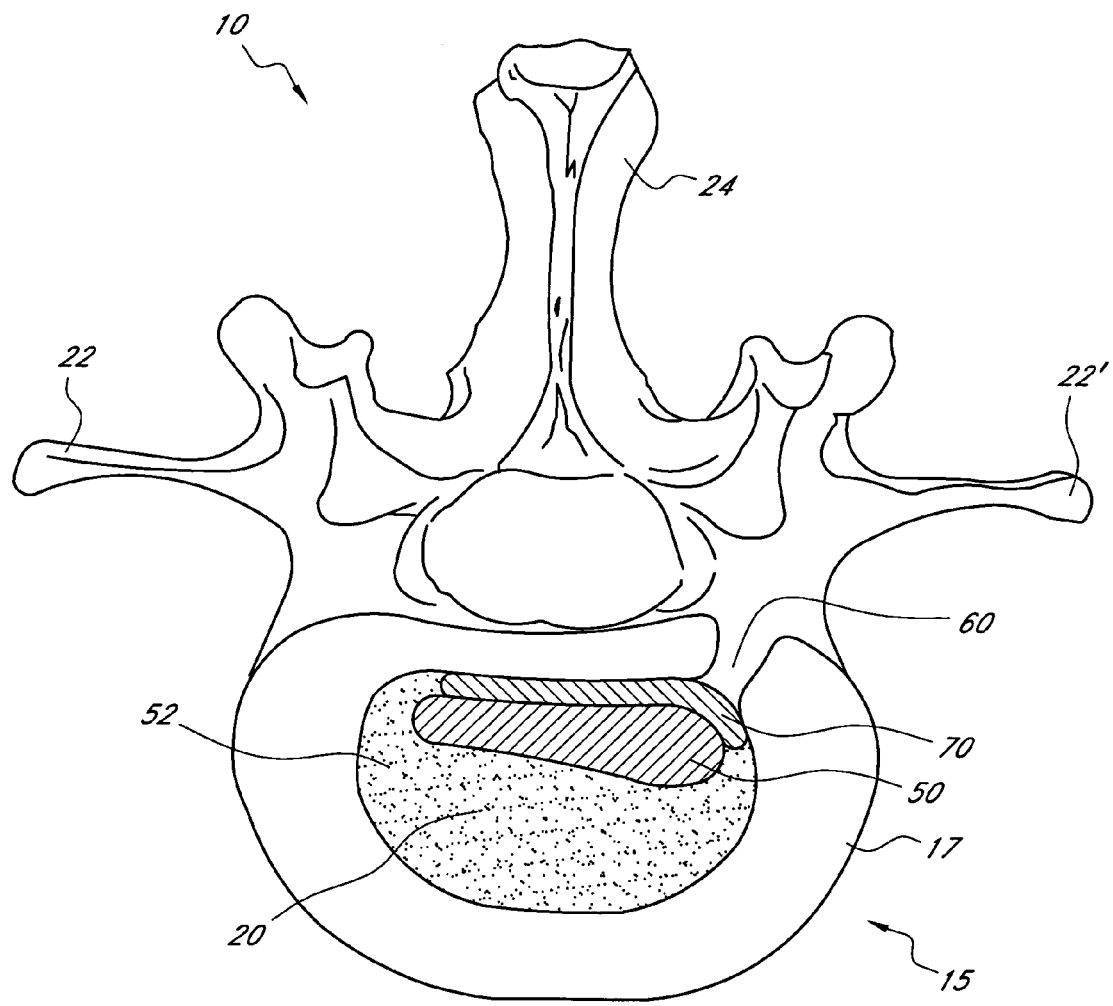
FIG. 10 is a cross-sectional view of a portion of a functional spine unit showing the prosthesis cooperating with a barrier according to another aspect of the invention.

As shown in FIG. 10, and as described in one or more of the above-mentioned patents or application, the barrier 70, if used, may be sized to sufficiently cover the defect or access opining 60 and reduce the likelihood of the barrier 70 extruding or slipping from covering the access opening 60. The barrier 70 may be sized, such that at least some portion of the barrier abuts the AF surrounding the access opening 60. The barrier 70 may act to seal the opening 60, recreating the closed isobaric environment of a healthy disc. The barrier 70 also may be affixed to tissues within the functional spinal unit or to the AF surrounding the opening 60. Such attachment may be facilitated with the use of sutures, staples, glues or other suitable fixation means or fixation devices.

Figure 11:
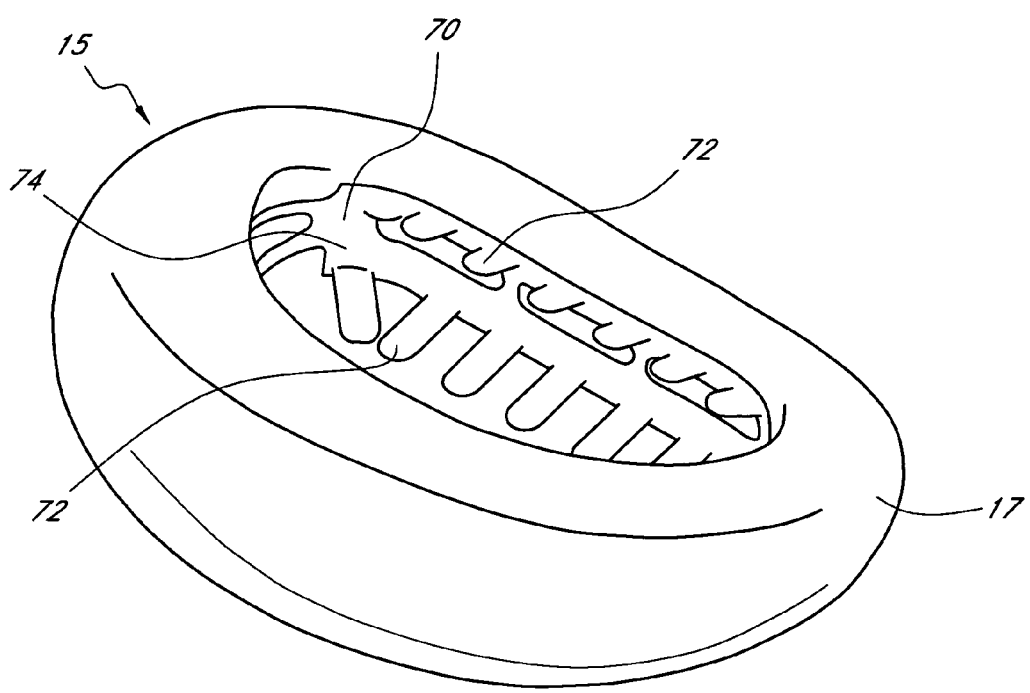
FIG. 11 is diagrammatic representation of the vertebral disc showing a barrier positioned within the interior region of the disc.

In use, the pressurized disc tissue and prosthesis 50 applies force on the inwardly facing surface of the barrier 70. This pressure may be exploited by the design of the barrier to reduce the likelihood of it dislodging or moving from its intended position. One exemplary barrier is shown in FIG. 11, where the barrier 70 includes inwardly facing surfaces 72 that expand upon the application of pressure. As the barrier expands, it becomes less likely to be expelled from the disc. The barrier 70 may be formed with a concavity facing inwardly to promote such expansion. In addition, as shown in FIG. 10, the prosthesis material 50 typically is positioned adjacent to the barrier 70 such that the likelihood of natural NP escaping through the access opening 60 is further minimized.

The barrier may be flexible in nature. It can be constructed of a woven material such as Dacron or Nylon, a synthetic polyamide or polyester, a polyethylene, or can be an expanded material, such as expanded polytetrafluroethylene (e-PTFE). The barrier may also be a biologic material such as cross-linked collagen or cellulous.

The barrier typically is a single piece of material, and may be expandable or include a component that allows it to be expanded from a compressed state after insertion into the interior of the disc. This expansion may be active, such as a balloon, or passive, such as a hydrophilic material. The expansion may also occur via a self-expanding deforming barrier or by incorporating such a material, such as a shape-memory material, for example. In the example shown in FIG. 11, the barrier 70 includes a cage 74 formed from a shape-memory material, such as nitinol. A cover (not shown) may be employed over the cage 74.

When a phase changing prosthesis material is used, the barrier or other annulus augmentation may be permanently implanted or used only temporarily until the desired phase change has occurred. For example, a sufficient amount of fluid or liquid prosthesis 50 may be implanted into the disc. Barrier 70 is then implanted to occlude the access opening 60. The prosthesis 50 is then cured or dried (or otherwise allowed to cure or dry) to a solid or semi-solid state, wherein the resulting prosthesis form is larger than the access opening. The barrier 70 then may be removed, as, due to the resulting size and/or shape of the prosthesis, the likelihood of the prosthesis escaping back through the access opening 60 is low.

As discussed above, the prosthesis 50 typically is placed within the interior region 52 of the vertebral disc 15 by a delivery device. Examples of suitable delivery devices are shown in FIGS. 12-22 In one illustrative embodiment, the delivery device 80 comprises a body 82 defining a longitudinal axis 83. The body 82 may be formed as an elongate cannula or other hollow tubular sleeve. The body 82 includes a proximal end 81 and a distal end 84, which is adapted to pass through the access opening 60 in the AF and deploy prosthesis 50 into the interior region 52. The distal end 84 may be rounded (not shown) to limit any damage to the AF or other anatomical structure. A push rod or plunger 86 is axially slidable within the cannula 82 and together with the end portion 84 of the cannula defines a holder region 87. The plunger 86 includes an end 89 that acts on the prosthesis 50 to dislodge the prosthesis from the holder region 87. The plunger 86 is pushed in the direction of arrow A shown in FIG. 12B to eject the prosthesis 50 from the holder region 87.

The plunger is axially slidable within the body so as to dislodge the prosthesis material therefrom. As shown for example in FIGS. 12A-12C, in one embodiment, the body 82 includes a first handle 160 or region to allow the surgeon to grasp the outside of the body. The plunger 86 includes a second handle 162, allowing the surgeon to actuate the plunger 86 to dislodge the prosthesis material 50.

The prosthesis material 50 may be inserted into the holder region 87 of the deployment device 80 using any suitable means. In this manner, a single use deployment device may be provided. In one embodiment, the deployment device may be preloaded with a desired amount of prosthesis material. In other embodiments, the deployment device may be placed in a vat of prosthesis material and actuated, in a manner similar to a syringe, to draw the prosthesis material into the deployment device. Alternatively, a surgeon or other assistant may place a desired amount of the prosthesis material within the deployment device. Of course, it should be appreciated that the present invention is not limited in this respect and that any suitable means or method for inserting the prosthesis may be used. And, the chosen means or method may depend upon the type of prosthesis material employed.

In one embodiment, any of the deployment devices and/or the prosthesis described herein may be supplied in a kit. The kit may include one or more of the same or different prostheses or components and/or one or more of the same or different deployment devices. The kit may include materials or devices to be used with the prosthesis. For example, the kit may include the above-mentioned therapeutic agents or agents to cure the prosthesis, if a curable prosthesis is employed. Also, the kit may include components, devices or other materials to aid in deploying the prosthesis. The kit further may include one or more of the same or different barriers. The kit also may include monitoring devices to monitor the amount of prosthesis being deployed and also may include instructional information, including any of the methodologies described herein. It should be appreciated that the present invention is not limited in this respect, as the herein noted or other suitable components or devices may be supplied with the kit.

Figure 12A:
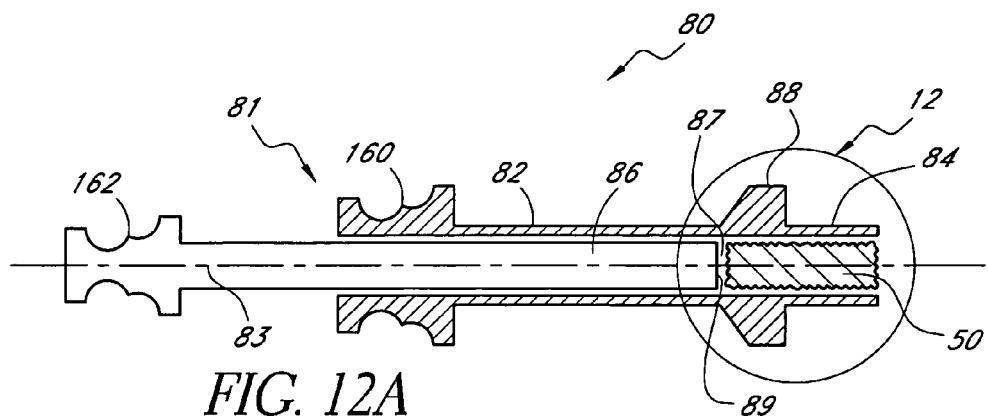
FIGS. 12A through 12C are cross-sectional representations of a deployment device used to deploy the prosthesis according to one aspect of the invention.
Figure 12B:
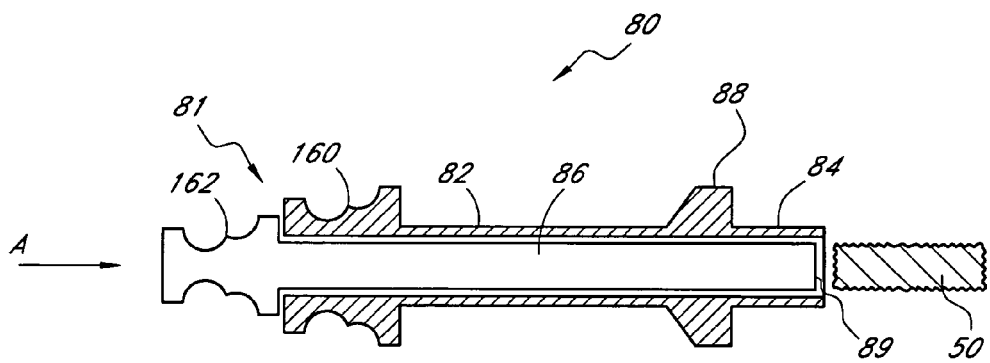
Figure 12C:
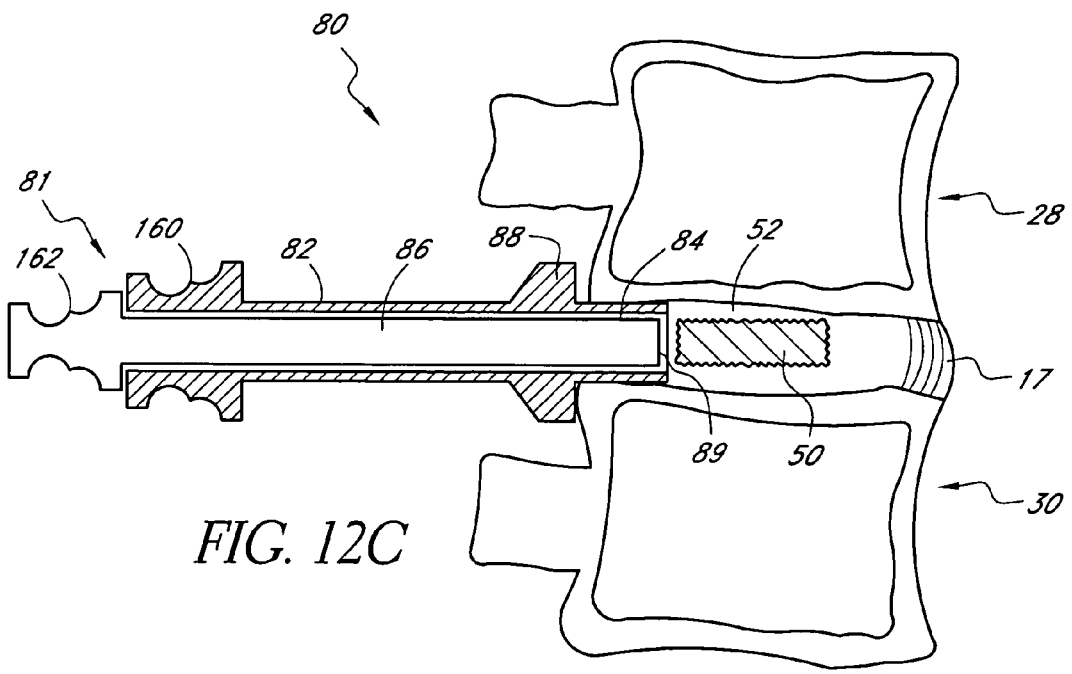

In some instances, it may be desirable to locate the prosthesis material within a certain position in the interior region of the vertebral disc. Thus, in one illustrative embodiment as shown in FIGS. 12A-12C, the deployment device includes a depth stop 88 that limits how deeply into the interior region of the vertebral disc the prosthesis is placed. For example, the depth stop 88 may seat against the vertebral bodies 28, 30, as shown in FIG. 12C, or the AF 17. In this manner, the tip 84 of the delivery device 80 is inserted into the access opening 60 in the AF until the depth stop 88 contacts the outer layer of the AF to prevent further insertion of the tip of the delivery device into the interior region of the vertebral disc. Once in this position, the delivery device is actuated to deliver the prosthesis 50 to the desired location. Although in this embodiment the depth stop 88 abuts the vertebral body to limit the insertion depth, the delivery device may be configured such that the depth stop abuts other anatomical features. For example, the depth stop may be located on a delivery device such that it is adapted to contact the AF or other bone or tissue located in the region.

Figure 13:
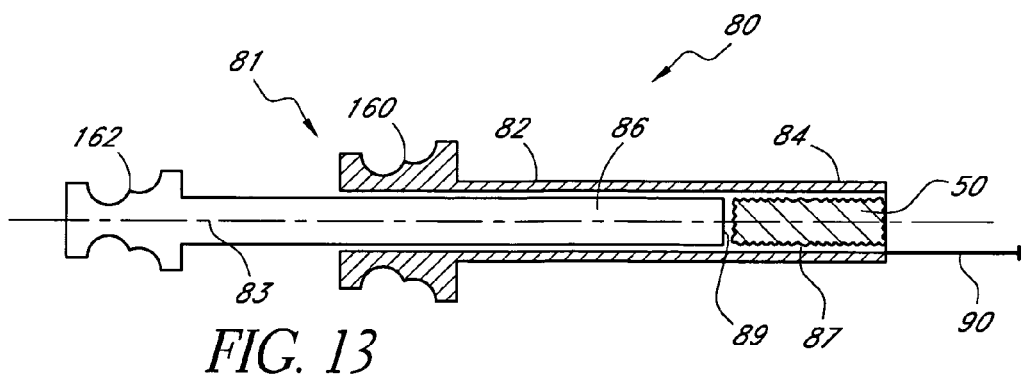
FIG. 13 is an alternative embodiment of the deployment device shown in FIGS. 12A-12C.

In the embodiment shown in FIGS. 12A-12C, the depth stop 88 is located on the outside of the delivery device. However, in other embodiments, an example of which is shown in FIG. 13, it may be desirable to configure the delivery device 80 with an internal depth stop 90. In this manner, the tip of the delivery device is placed through the access opening in the AF and is advanced until the internal depth stop 90 contacts the opposite wall of the AF or other structure within the interior region of the vertebral disc. Once the tip is in the proper position, the delivery device is actuated to deploy the prosthesis material at the suitable location within the interior region of the vertebral disc.

Figure 14A:
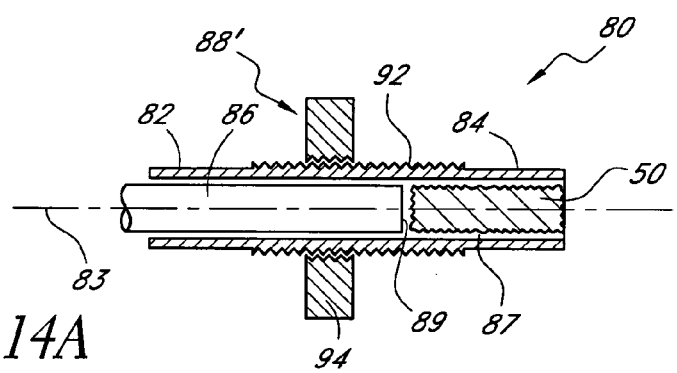
FIGS. 14A-14D show alternative embodiments of a portion of the deployment device encircled by line 14 of FIG. 12A.

The depth stop also may be adjustable, giving the surgeon the flexibility to locate the prosthesis in any desired position. In one example, as shown in FIG. 14A, the body 82 may include a threaded section 92 and a depth stop 88' may be formed as a threaded ring 94 that engages the body 82. By rotating the ring 94 relative to the body, the location of the depth stop may be adjusted.

Figure 14B:
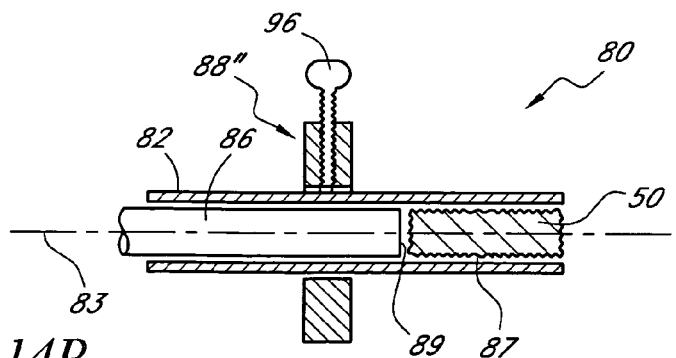
Figure 14C:
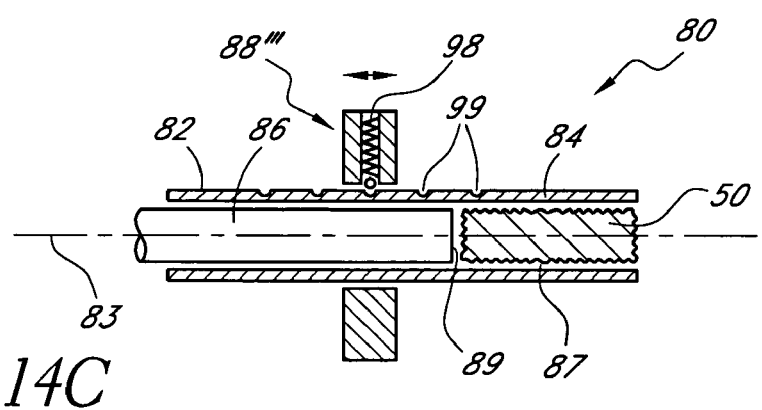

Although a thread is shown and described, other suitable adjustment mechanisms may be employed. For example, as shown in FIGS. 14B and 14C, a depth stop may be slidingly engaged on the body 82 and locked in a position using a suitable locking device, such as a clamp or thumb-screw 96 for a depth stop 88" shown in FIG. 14B, ball 98 and detent 99 mechanism for a depth stop 88''' shown in FIG. 14C, or other ratcheting-type mechanisms.

Figure 14D:
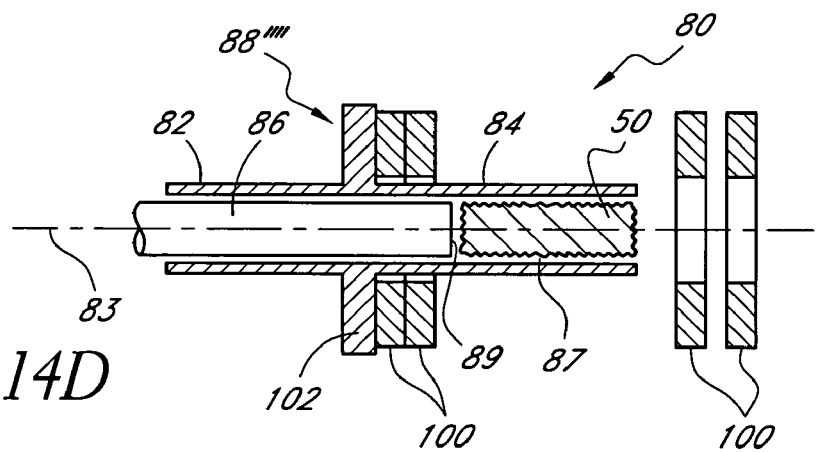

In another embodiment, as shown in FIG. 14D a depth stop 88'''' is formed as a plurality of washer-like rings 100 that can slip over the body and abut a fixed depth stop 102. In this manner, the depth may be set by adding rings onto the body until the desired depth is achieved. The rings may be locked in position or freely retained on the body.

Figure 15:
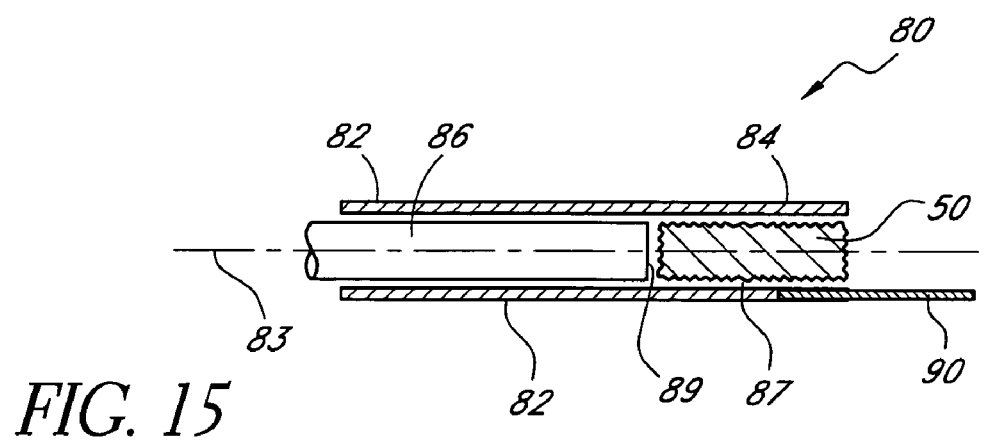
FIG. 15 is a cross-sectional representation of a portion of the deployment device showing yet another alternative embodiment to the invention.

An internal depth stop may be adjustable providing the desired flexibility as to where to locate the prosthesis. One example is shown in FIG. 15, in which a depth stop 90' is threaded into a wall of the body 82 to enable depth adjustment in a telescoping manner.

Figure 16:
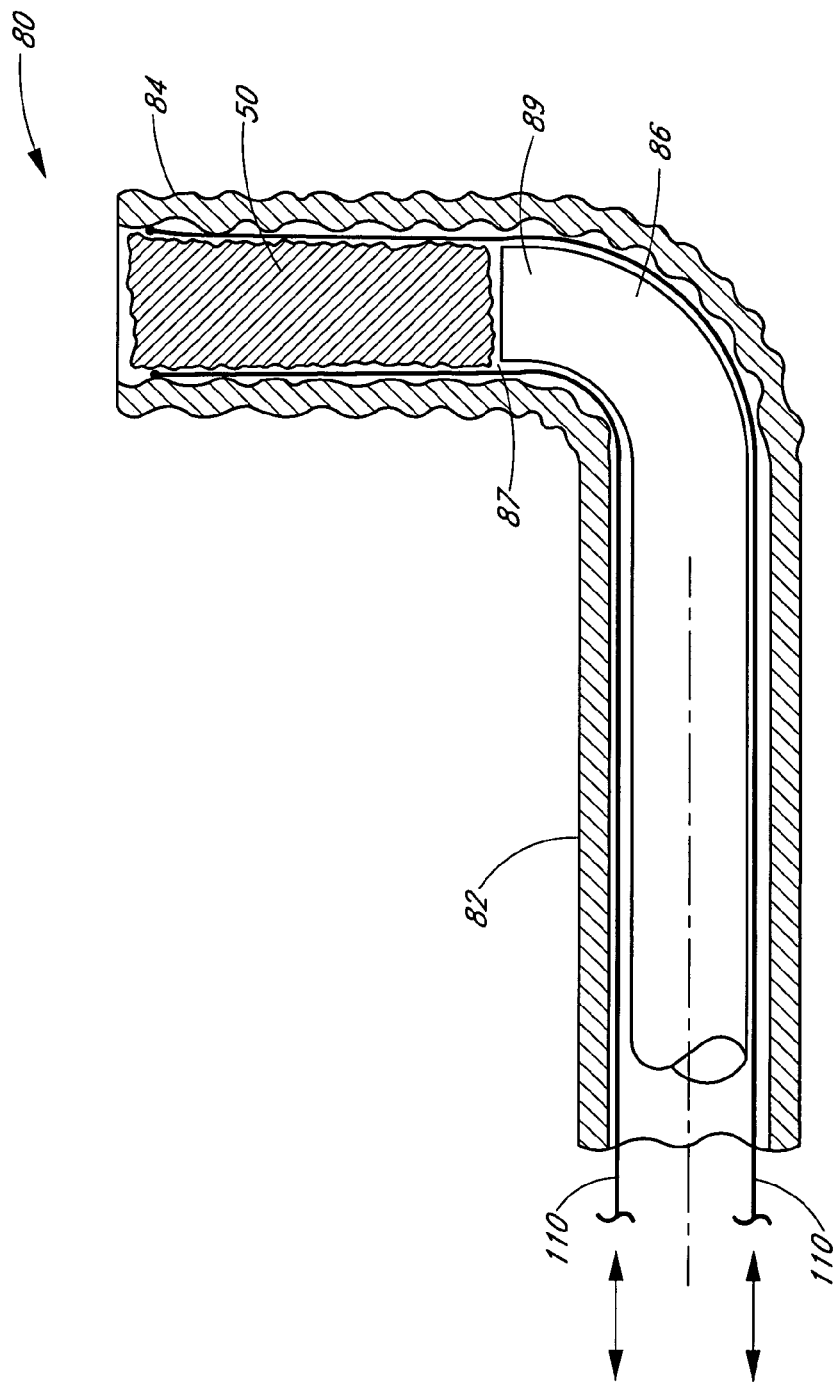
FIGS. 16 and 17 are cross-sectional views of a portion of the deployment device according to alternative embodiments of the invention.

To further enhance placement of the prosthesis in a desired location within the interior of the vertebral disc, the delivery device 80 may include a curved or otherwise articuatable end 84 that can be either actively or passively manipulated to alter its position, as shown in FIG. 16. With a deployment device having a straight end as shown, for example, in FIG. 12A, the prosthesis may only be deployed along the longitudinal axis of the delivery device. In embodiments employing a curved or articuatable end, the prosthesis may be deployed at any desired angle relative to the longitudinal axis. For example, the prosthesis may be deployed adjacent one of the endplates, in the middle of the interior region of the vertebral disc, or adjacent the AF.

One illustrative embodiment of an articulatable end is shown in FIG. 16. Guide wires 110 are fixed to the tip 84 of the delivery device, and in one embodiment, the guide wires 110 are anchored using suitable anchors, such as eyelets, in the interior region of the body 82. The wires 110 extend internally through body 82 toward the proximal end 81 of the body 82 and exit end 81. Retracting the wires 110 causes the tip 84 to articulate relative to the longitudinal axis of the delivery device. Other mechanisms for causing the tip to curve or bend may be employed. To provide for an articulating end, the distal end 84 is formed of a flexible material or in a flexible configuration.

Figure 17:
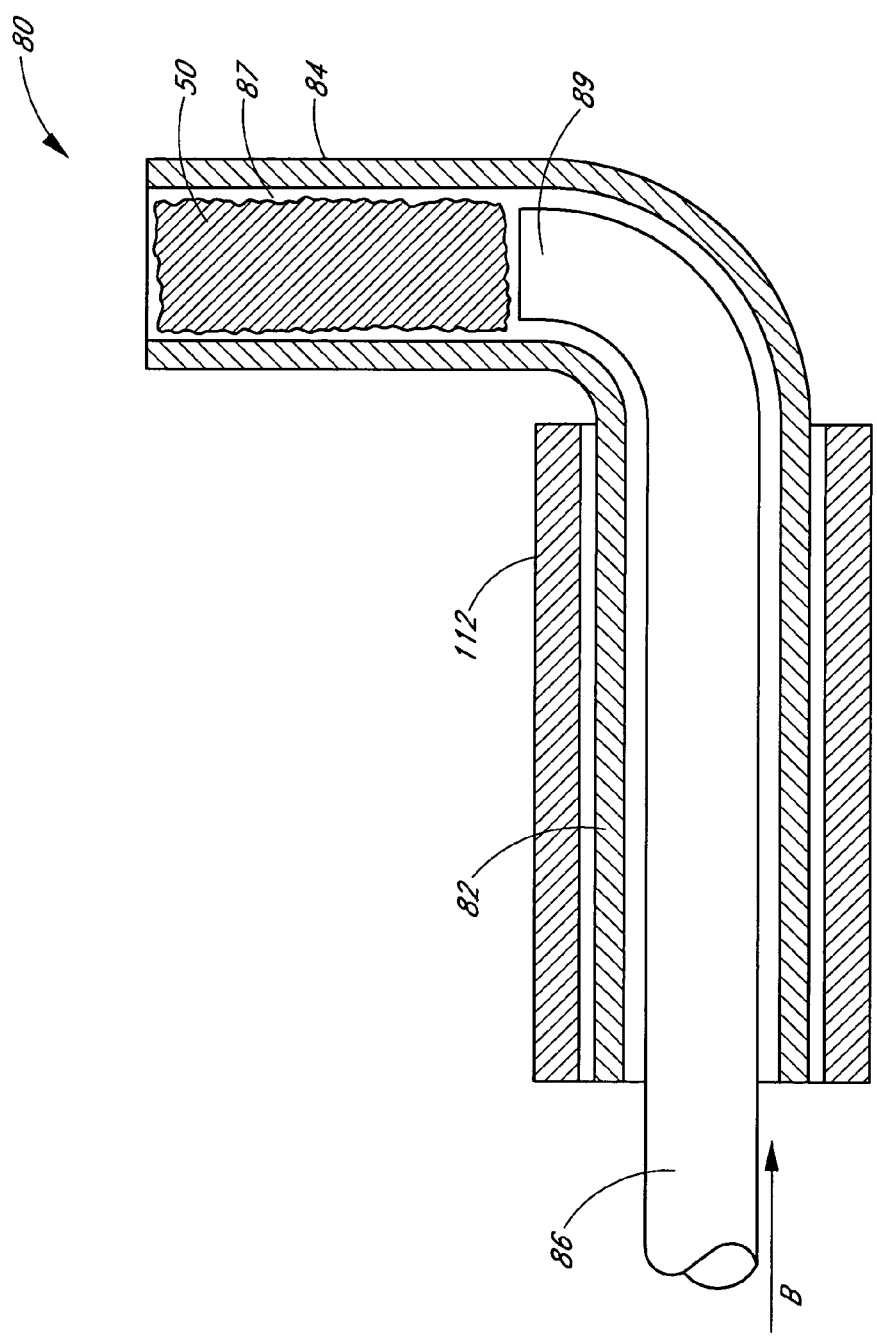

In another embodiment, rather than actively deforming the tip of the delivery device, the tip itself may be configured such that it bends into a predetermined configuration upon insertion. For example, the tip of the delivery device may include a kink point or a change in the stiffness along the length of the tip that causes the tip to assume a predetermined configuration. In one embodiment, as shown in FIG. 17, the delivery device 80 includes a relatively stiff outer tubular member 112 that contains the body 82. Further, body 82 may be formed of, or otherwise include, a relatively flexible material, such as a spring member, that holds the tip in a bent configuration. When inside the sleeve 112, the tip is retained in a straight configuration to allow insertion into the vertebral disc. When body 82 is displaced with respect to member 112 in the direction of arrow B, the tip 84 emerges from the sleeve 112 and assumes its bent configuration, as shown.

When a curved or otherwise articuatable end is employed, plunger 86 should be sufficiently flexible to conform to the shape of the tip of the delivery device when in its bent configuration so as to be able to dislodge the prosthesis material.

In some circumstances, it may be desirable to place the prosthesis at a desired location within the interior region of the vertebral disc upon retracting a portion of the delivery device rather than by extruding the prosthesis material from the delivery device 80, as in the embodiment shown in FIGS. 12A-12C. Thus, in this embodiment shown in FIGS. 18A-18C, and FIG. 19, a retrograde delivery device 80 is shown, wherein the body 82 is retracted in the direction of arrow C (see FIG. 18B) relative to the plunger 86. Once the prosthesis material has been deployed within the interior region, the delivery device may be removed from the vertebral disc.

The delivery device of this embodiment may also include a curved or articulatable end as described above and/or a depth stop, whether or not adjustable, to place the prosthesis at the desired location.

Figure 18A:
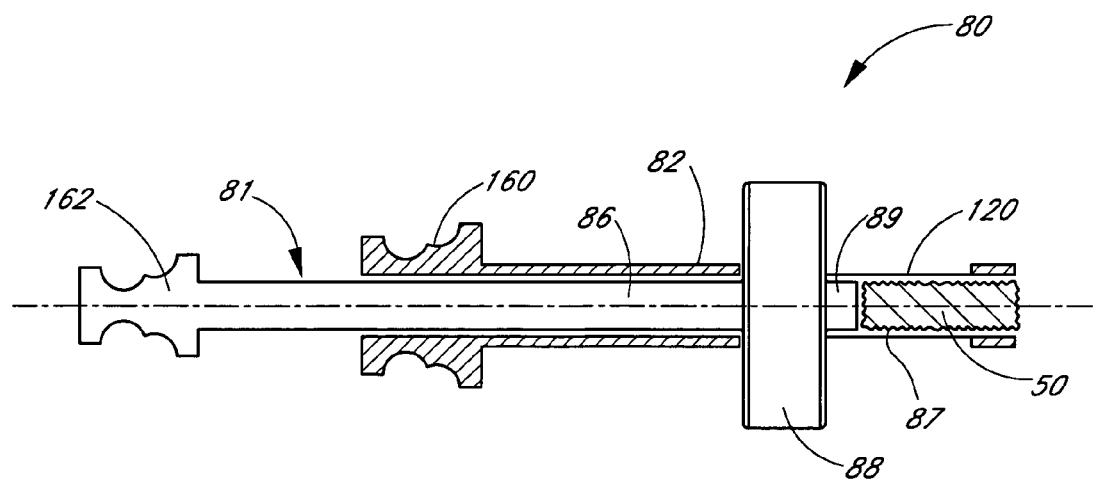
FIGS. 18A-18C are cross-sectional representations of deployment device according to an alternative embodiment of the invention.
Figure 18B:
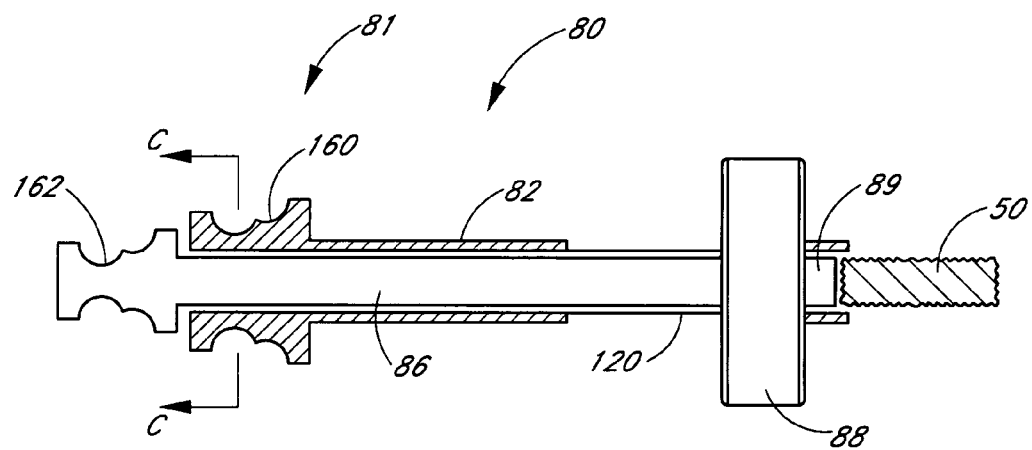
Figure 18C:
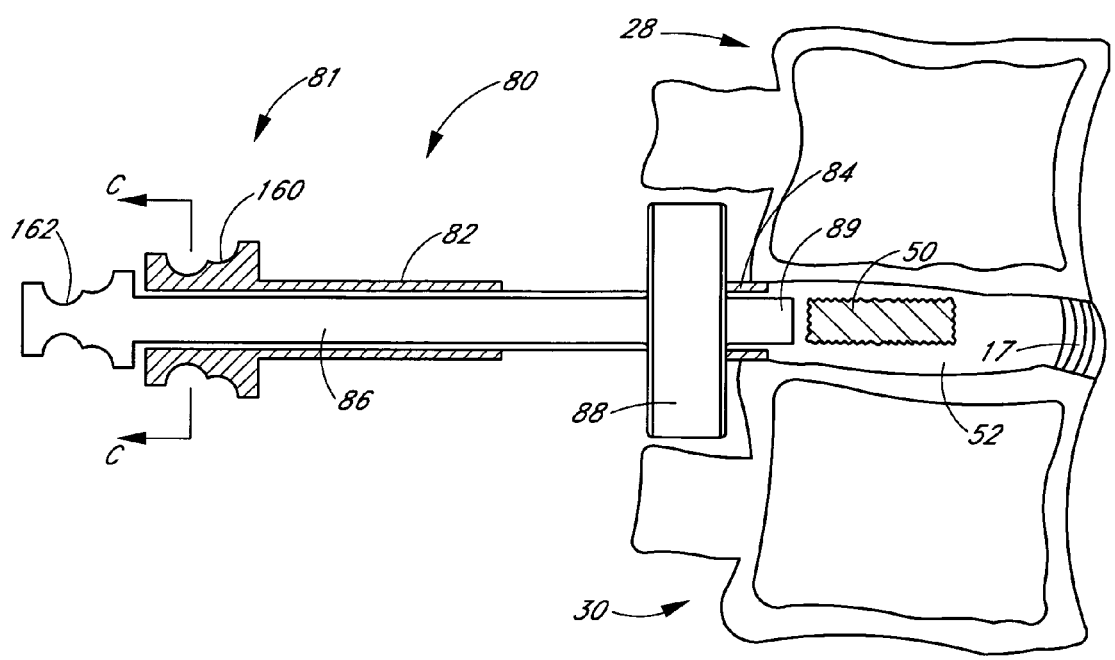
Figure 19:
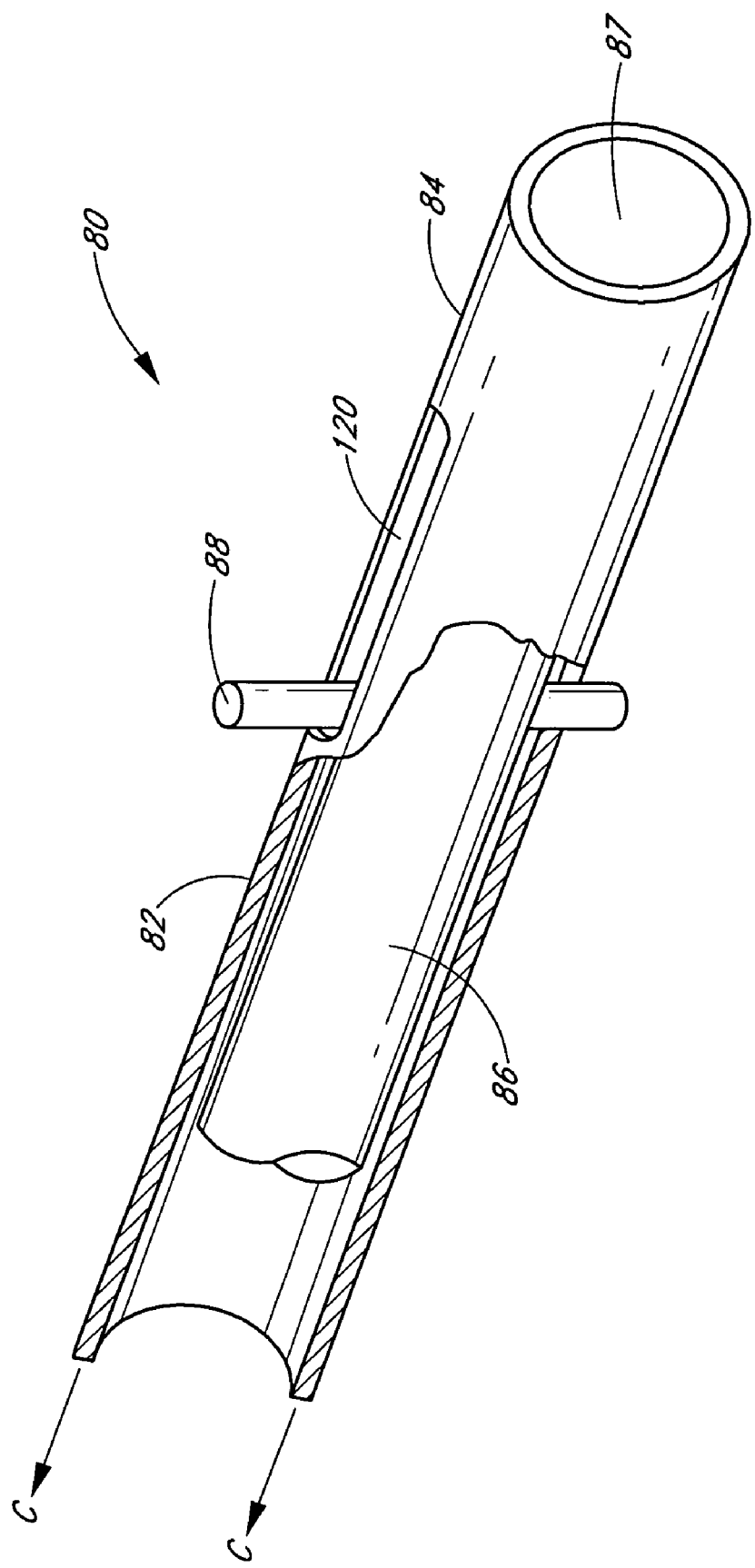
FIG. 19 is a diagrammatic prospective view of a portion of the deployment device shown in FIGS. 18A-18C.

As shown in FIGS. 18A-18C, the delivery device may include a depth stop 88. To provide the depth stop 88 while allowing the body to be retracted along arrow C as described, the body includes a slot 120, as shown in FIG. 19. Thus, the tip 84 of the delivery device is inserted into the interior region of the vertebral disc until the depth stop 88 contacts the desired anatomy. Then, the body 82 may be retracted along arrow C while the depth stop 88 is held against the anatomy. The slot 120 in the body 82 allows the body 82 to be retracted such that the stop 88 may move relative to the body 82 within the slot 120.

As discussed above, the prosthesis may be formed of any suitable material including solids, semi-solids or even materials in liquid or fluid form. However, injecting a fluid or liquid prosthesis material may increase the risk of adding localized pressure as the fluid works its way through the interior region of the vertebral disc, which may result in damage to the disc. In addition, merely injecting the fluid into the interior region can result in imprecise placement within the interior region or possibly inadvertently deliver the material into undesired locations, such as near the endplates or at fissures or tears in the AF, all potentially increasing the likelihood of pain or reducing the effectiveness of the prosthesis.

In one embodiment as shown in FIG. 20A, the delivery device 80 is adapted to deliver a prosthesis that is in fluid or liquid form. In this embodiment, end 84' is generally closed, but includes perforations 132 and the prosthesis is held within holder region 87. Upon advancing the plunger 86, the liquid or fluid prosthesis material within the holder 87 is extruded, ejected or otherwise dispensed through the perforations 132 in the direction of arrow D.

The perforations formed in the tip may be any suitable perforations including holes, as shown, or other openings. Alternatively, as shown in FIG. 20B, the perforations may be in the form of fins 132' that direct the liquid or fluid prosthesis material in the direction of arrow D'. In one embodiment, the delivery device includes perforations extending only radially outwardly. In this manner, direct pressure through the end of the delivery device onto the NP or locating the prosthesis in an otherwise undesirable location may be avoided.

Figure 21A:
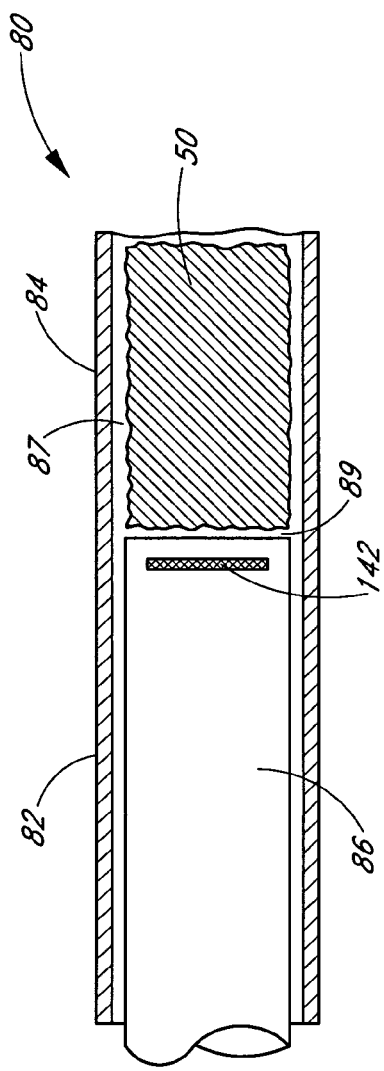
FIGS. 21A and 21B are diagrammatic cross-sectional representations of alternative embodiments of the deployment device.
Figure 21B:
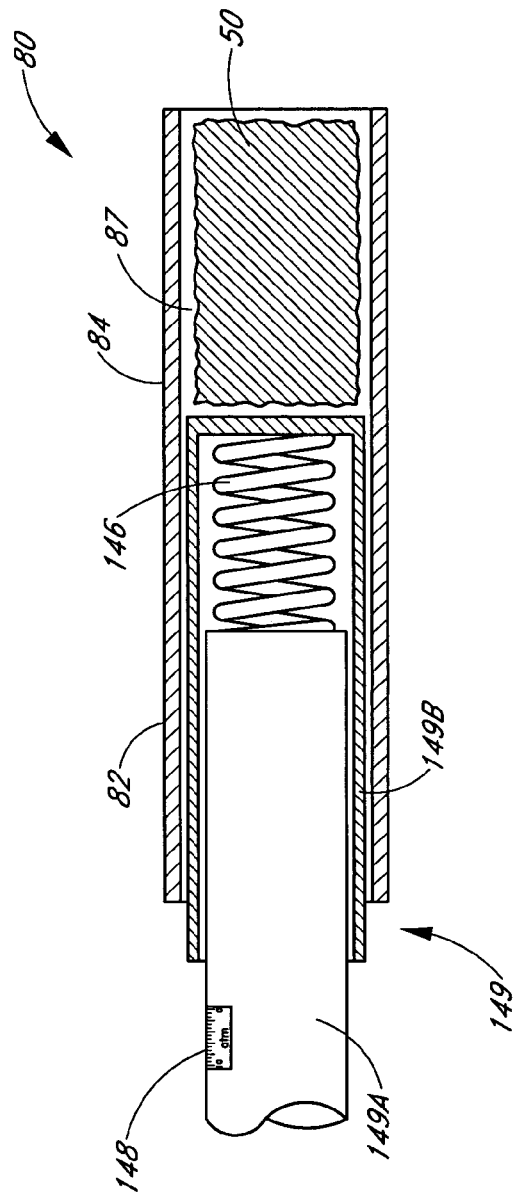

In another embodiment, the deployment device monitors the amount of material being delivered. In one illustrative embodiment as shown in FIGS. 21A-21B and 20, the delivery device 80 includes a gauge 140 such that the surgeon, for example, may quickly determine the amount of prosthesis material being deployed from the delivery device. In one embodiment, the gauge 140 may be a pressure gauge that may be used to determine the increase in pressure within the vertebral disc as the prosthesis material is being deployed. In one embodiment as shown in FIG. 21A, the gauge may include a pressure sensitive transducer 142 disposed on or within the plunger 86 and suitable electronics (not shown) to record and measure the pressure within the disc. The pressure transducer may be situated on the delivery device such that it records the resistance to insertion force. The resistance force is correlated to the pressure increase within the vertebral disc such that the surgeon would know when enough prosthesis material has been deployed. The pressure also may be determined with the use of a suitably placed strain gauge.

Alternatively, the gauge may be a mechanical gauge 144 as shown in FIG. 21B, that employs a spring 146 and an indicator 148 coupled to the spring that moves in response to the resistance to insertion force. Again, the resistance force may be correlated to the increase in pressure in the interior region of the disc such that when a certain resistance force is obtained, further insertion of prosthesis material may be terminated. In this embodiment, the plunger 149 is formed as a two-part plunger having a first plunger 149A and a second plunger 149B. Spring 146 is disposed between the two plungers. Moving plunger 149A causes spring 146 to compress and act on plunger 149B, which in turn dislodges prosthesis 50. As the resistance to insertion increases, plunger 149A moves further into plunger 149B and a higher pressure reading is indicated at indicator 148. It should be appreciated that the present invention is not limited to any particular gauge as any suitable gauge may be employed to determine the increase in pressure in the interior region of the vertebral disc.

Figure 22:
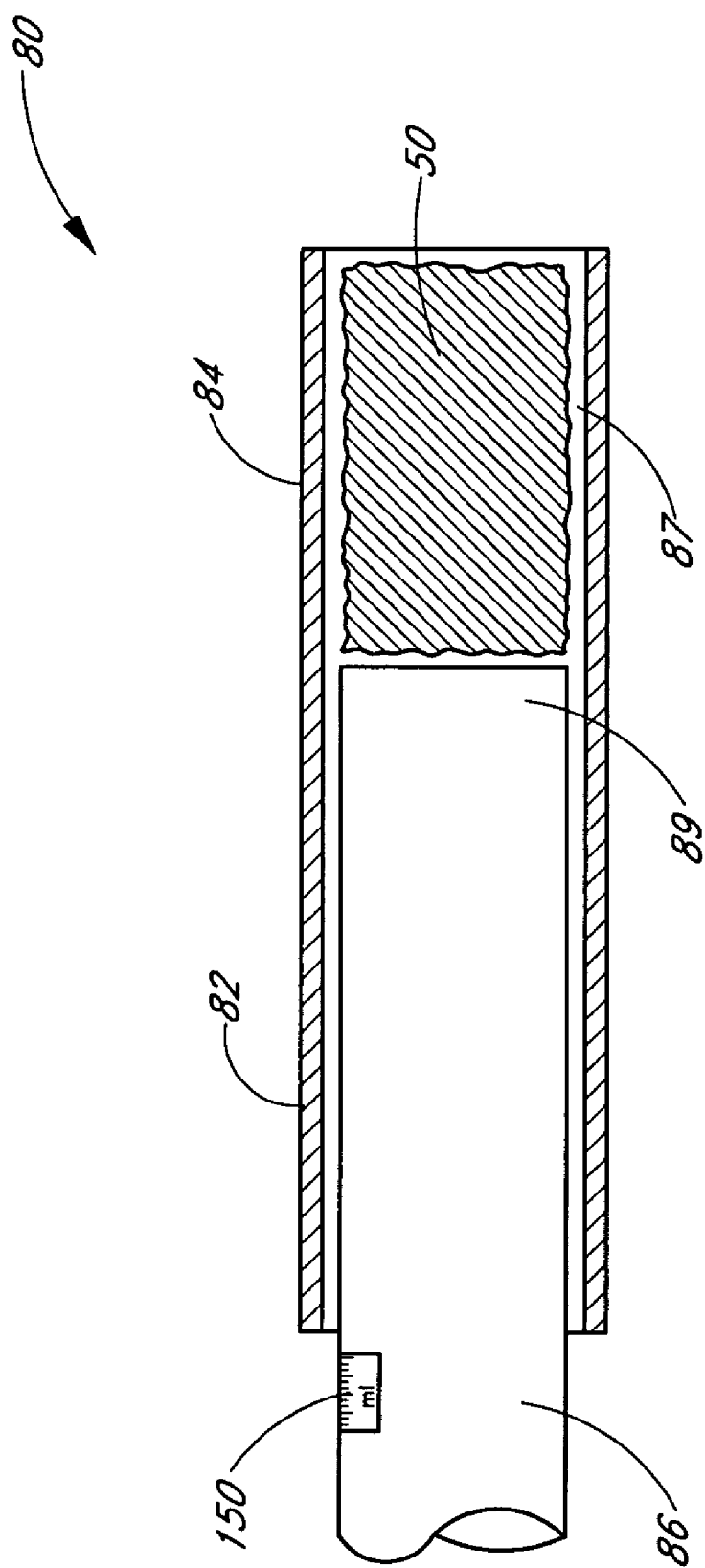
FIG. 22 is a diagrammatic cross-sectional representation of yet another alternative embodiment of the deployment device.

In another embodinent as shown in FIG. 22, the gauge may be a volume gauge 150 to indicate the volume of prosthesis material being delivered to the interior region of the vertebral disc. In this respect, the delivery device may be configured similar to a syringe and includes a series of lines on the body that correlates to the volume of material being deployed.

In yet another embodiment (not shown), a combination of gauges may be employed. For example, a deployment including both a pressure gauge (such as pressure transducer 142) and a volume gauge (such as indicator 150) may me employed.

The delivery device 80 may be formed from any suitable material, as the present invention is not limited in this respect. Thus, the delivery device may be formed from a plastic material, such as a polycarbonate, or a metal material, such as stainless steel, or any suitable combination of materials. In addition, the delivery device may be formed of a material that can be readily sterilized. Further, the delivery device may be formed as a single use device such that resterilization is not required after use.

In another embodiment, in addition to the shapes described above, the prosthesis may include a grouping of multiple components of the same or different shapes that can be inserted into the interior region of the vertebral disc as a group. By grouping smaller discrete component prostheses together, the prosthesis may perform differently than a single unit which can be advantageous. The volume of an individual component prosthesis can range between approximately 10 mm$^3$ and approximately 500 mm$^3$. Each component of the group, or at least one component, may be formed of the same or different materials or material characteristics as other components of the group, such as those materials or characteristics described herein, as the present invention is not limited in this respect.

The delivery device 80 may deploy the grouping of prosthesis components of any desired shape. When delivering a grouping of components, each (or at least one) prosthesis component may be in the form of spheres or beads (see FIG. 8), rods or spirals (see FIG. 9), geometric solids, irregular solids, sheets or any other suitable shape disclosed herein or otherwise formed. The components typically are deployed in a group and in a single step. At least one component prosthesis from the group, or the entire group, may be deployed to any desired location, examples of which are discussed above. In one embodiment, the grouping includes at least two components forming the prosthesis. In another embodiment, the grouping includes at least three components forming the prosthesis. Other suitable grouping sizes, such as four, five and six, may be employed, as the present invention is not limited in this respect. In one embodiment, the multi-component prosthesis can, for example, comprise hydrogel spheres, that can be extruded, ejected or otherwise dispensed from the delivery device, thereby displacing, without removing, autologous vertebral tissues. As is apparent from the above discussion, the size of the group may depend upon certain factors. For example, as is apparent from the above discussion, the group size may be a function of the desired disc height, the desired disc pressure or the desired disc volume, such as the desired augmentation volume.

Figure 23A:
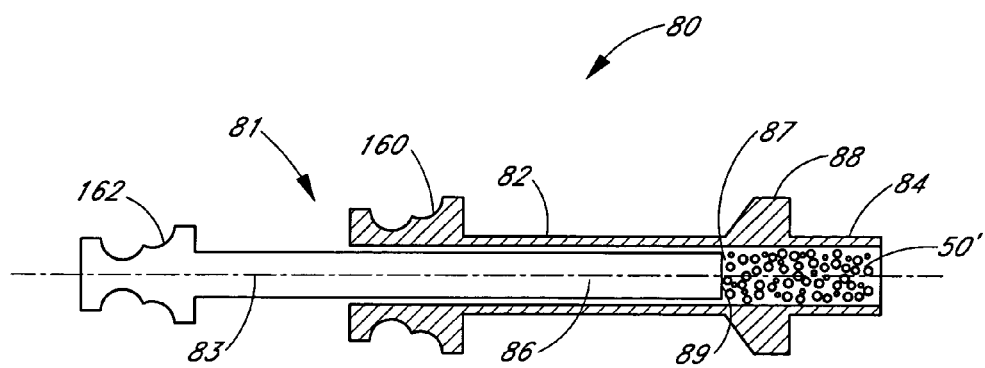
FIGS. 23A through 23C are cross-sectional representations of a deployment device used to deploy the prosthesis according to one aspect of the invention.
Figure 23B:
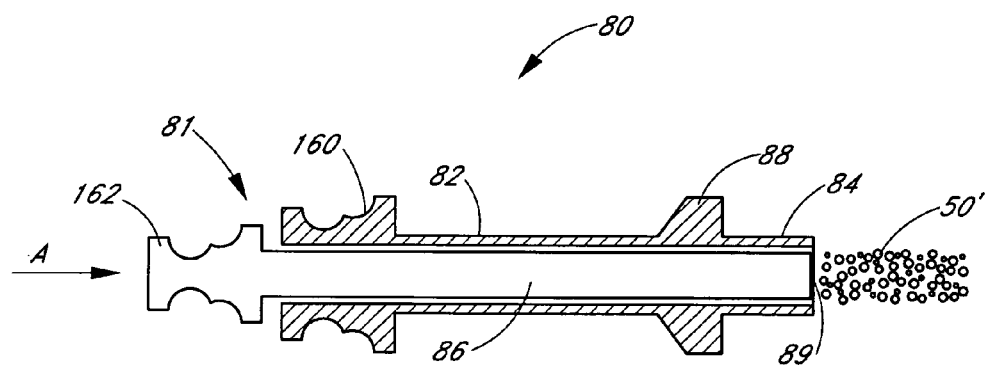
Figure 23C:
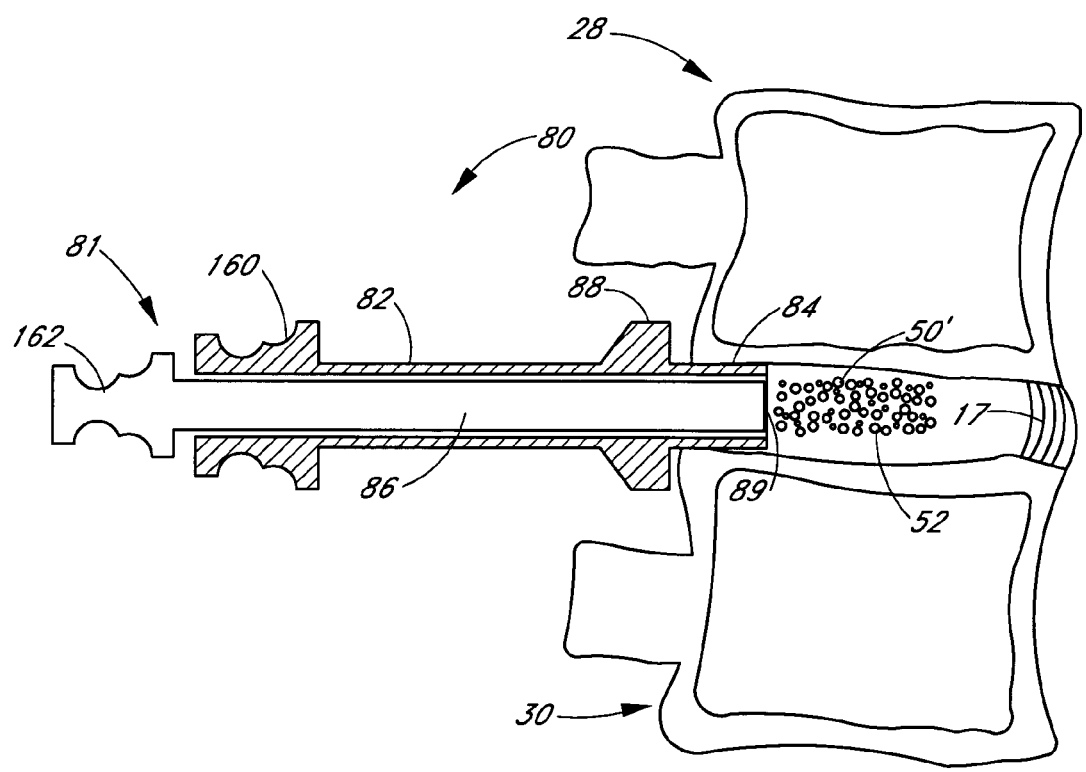

FIG. 23A is a cross-sectional view of a delivery device 80 loaded with a grouping of spherical or bead shaped prosthetic components 50' and with the plunger 86 in the retracted position. FIG. 23B shows the plunger 86 in the advanced position, with the components 50' of the prosthesis deployed as a group from the distal tip 84. FIG. 23C shows a view of two adjacent vertebral bodies 28, 30, with the tip 84 of the delivery device 80 inserted within the vertebral disc. Depth stop 88 is placed against at least a portion of the annulus or vertebral body. The plunger 86 is shown in the advanced position in which the prosthesis 50' has been delivered within the area bounded by the annulus, causing the tissues of the annulus, nucleus, or vertebral endplates to be displaced in relation to the amount of prosthesis added.

Figure 24A:
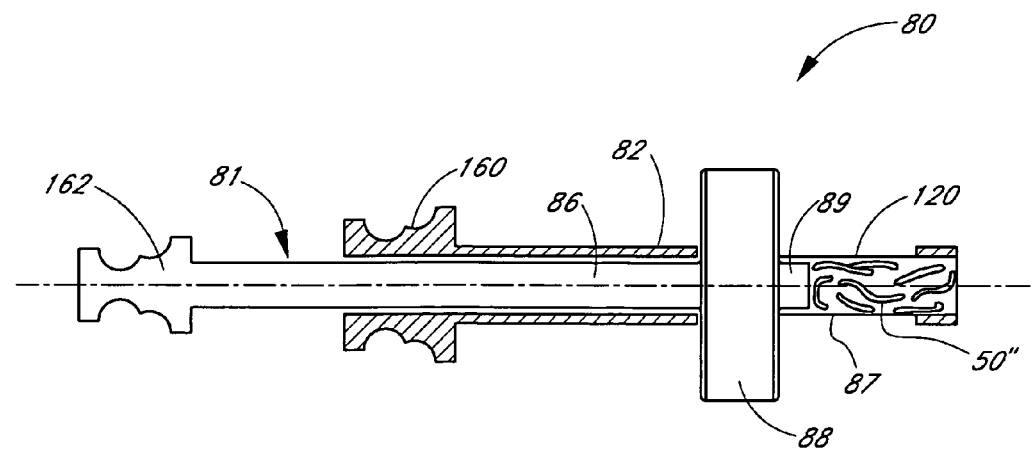
FIGS. 24A through 24C are cross-sectional representations of a deployment device used to deploy the prosthesis according to one aspect of the invention.
Figure 24B:
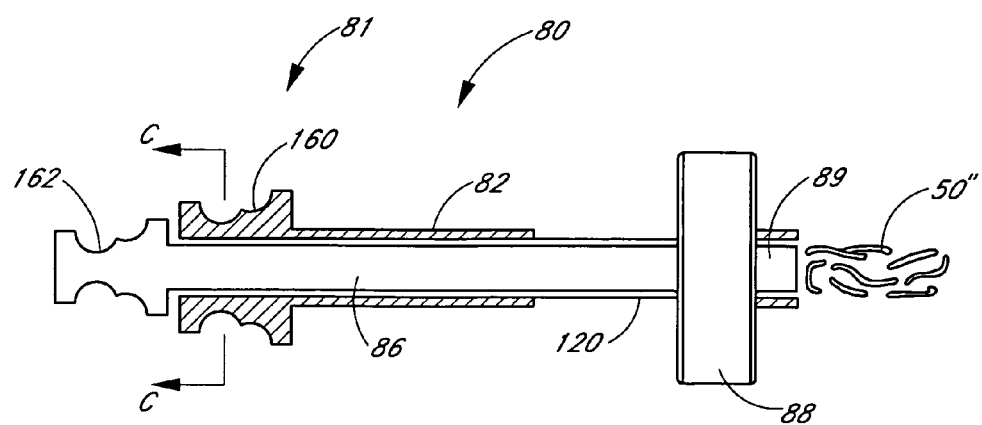
Figure 24C:
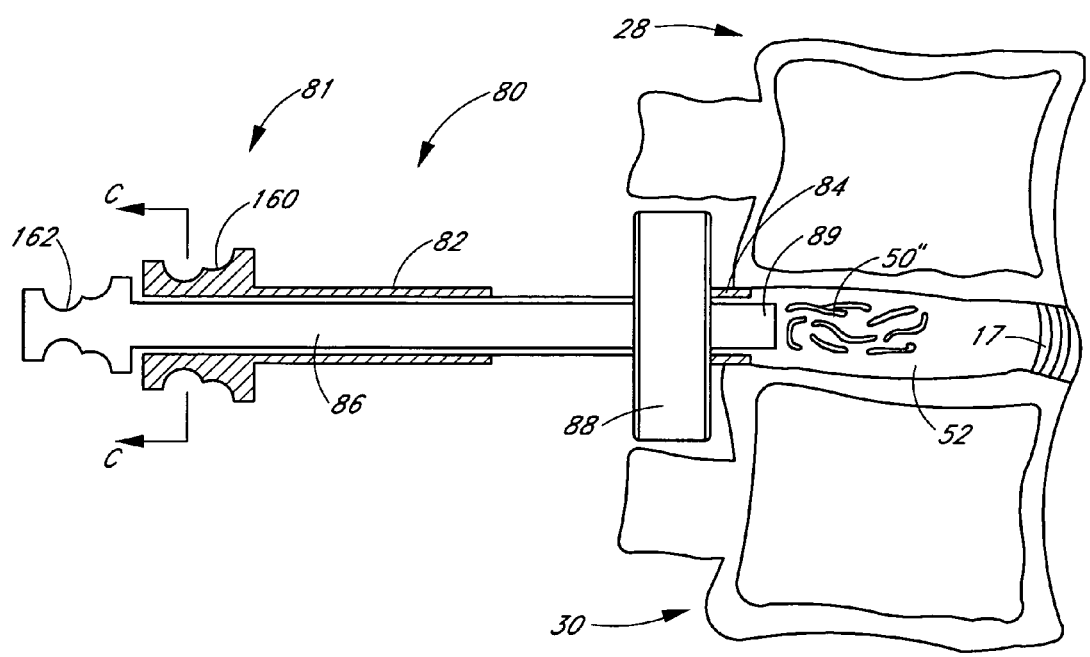

FIG. 24A is a cross-sectional view of a retrograde delivery device (such as that described above with respect to FIGS. 18A-18C), which is loaded with rod- or spiral- shaped prosthetic components 50" and with the body 82 advanced relative to the plunger 86. FIG. 24B shows the body 82 in the retracted position relative to the plunger 86, in which the components 50" of the prosthesis are deployed as a grouping from the distal tip 84. FIG. 24C shows a view of two adjacent vertebral bodies 28, 30, with the tip 84 delivery device 80 inserted within the vertebral disc. Depth stop 88 is placed against at least a portion of the annulus or vertebral body. The body 82 of the delivery device is shown in the retracted position relative to the plunger 86, with the prosthesis 50 delivered within the area bounded by the annulus, causing the tissues of the annulus, nucleus, or vertebral endplates to be displaced in relation to the amount of prosthesis added.

Although the spherical- or bead- shaped prosthesis 50' is shown in the delivery device of FIGS. 23A-23C and the rod- or spiral- shaped prosthesis 50" is shown in the delivery device of FIGS. 24A-24C, the present invention is not limited in this respect. Thus, the spherical- or bead- shaped prosthesis 50" may be deployed with any delivery device described herein or otherwise, including the delivery device shown in FIGS. 24A-24C and the rod- or spiral- shaped prosthesis 50' may be deployed with any delivery device described herein or otherwise, including the delivery device shown in FIGS. 23A-23C.

It should be understood that the foregoing description of the invention is intended merely to be illustrative thereof and that other embodiments, modifications, and equivalents of the invention are within the scope of the invention recited in the claims appended hereto. Further, although each embodiment described above includes certain features, the invention is not limited in this respect. Thus, one or more of the above-described or other features of the prosthesis, method of implantation, or delivery device, may be employed singularly or in any suitable combination, as the present invention is not limited to a specific embodiment.

What is claimed is:

1. A device for delivering a prosthesis material to an interior region of a vertebral disc, the device comprising:

a retractable body having a proximal end and a distal end;

a holder region disposed adjacent the distal end of the body, the holder region being adapted to hold the prosthesis material prior to delivery into the interior region of the vertebral disc;

a plunger disposed within the retractable body, the plunger and retractable body adapted to move relative to each other to release the prosthesis material;

a pressure transducer disposed on or within the plunger to sense a pressure parameter within the disc, wherein said pressure parameter is correlated to a pressure increase within the vertebral disc; and a stop disposed on the plunger, wherein the stop allows positioning of the retractable body relative to the interior region of the vertebral body such that the prosthesis material is released within the interior region of the vertebral body at a desired location, and wherein the retractable body comprises a slot that allows the retractable body to retract such that the stop moves relative to the plunger within the slot.

2. The device according to claim 1, wherein the stop is adjustable relative to at least the body.

3. The device according to claim 1, wherein the plunger comprises a first end defining a first handle adapted to be manipulated by a user, and a second end adapted to dislodge the prosthesis material from the holder region upon actuation of the first handle.

4. The device according to claim 3, wherein the body comprises an elongate hollow sleeve and wherein the plunger is axially slidable within the sleeve.

5. The device according to claim 4, wherein the sleeve defines a second handle, the second handle adapted to be grasped by a user such that the user can displace the first handle relative to the second handle.

6. The device according to claim 4, wherein the holder region is defined by the distal end of the elongate hollow sleeve.

7. The device according to claim 1, in combination with the prosthesis material.

8. The combination according to claim 7, wherein the device is pre-loaded with the prosthesis material.

9. The device according to claim 1, wherein the body comprises a hollow sleeve that is adapted to be retracted relative to the plunger to dispense the prosthesis material upon retraction of the sleeve.

* * * * *

UNITED STATES PATENT AND TRADEMARK OFFICE
CERTIFICATE OF CORRECTION

PATENT NO.        : 7,507,243 B2                                        Page 1 of 1
APPLICATION NO.   : 10/430902
DATED             : March 24, 2009
INVENTOR(S)       : Gregory H. Lambrecht et al.

It is certified that error appears in the above-identified patent and that said Letters Patent is hereby corrected as shown below:

On Page 1, under Item 63, Related U.S. Application Data, after "2001," please insert --now Pat. No. 7,258,700,--.

On Page 1, under Item 74, Attorney, Agent, or Firm, after "Kavanaugh", please insert --, Intrinsic Therapeutics--.

On Page 4, at Column 2, Line 34, in Item 56, under Other Publications, please change "Prothesis" to --Prosthesis--.

On Page 5, at Column 1, Line 27, in Item 56, under Other Publications, please change "Experimental" to --Experience--.

At Column 1, Line 12, please change "pending," to --U.S. Pat. No. 7,258,700,--.

At Column 8, Line 61, please change "tern" to --term--.

At Column 9, Line 13, please change "min." to --mm.--.

At Column 19, Line 19, please change "emdobinent" to --embodiment--.

At Column 21, Line 1, in Claim 1, please change "the body" to --the retractable body--.

Signed and Sealed this

Fifth Day of October, 2010

David J. Kappos
*Director of the United States Patent and Trademark Office*